(12) United States Patent
Cetti et al.

(10) Patent No.: US 11,844,854 B2
(45) Date of Patent: *Dec. 19, 2023

(54) FRAGRANCE MATERIALS

(71) Applicant: The Procter & Gamble Company, Cincinnati, OH (US)

(72) Inventors: Jonathan Robert Cetti, Mason, OH (US); Zerlina Guzdar Dubois, Mason, OH (US); Virginia Tzung-Hwei Hutchins, Cincinnati, OH (US); Michael Wayne Kinsey, Lebanon, OH (US); Christine Marie Readnour, Fort Mitchell, KY (US); Christelle Marie Sandrine Bonnet, Caillouet-Orgeville (FR); Lynette Anne Makins Holland, Abbots Langley (GB); Fabienne Pastor, Meriel (FR); Jose Maria Velazquez Mendoza, Ascot (GB); Jonathan Richard Stonehouse, Windlesham (GB); William Eoghan Staite, Egham (GB)

(73) Assignee: The Procter & Gamble Company, Cincinnati, OH (US)

( * ) Notice: Subject to any disclaimer, the term of this patent is extended or adjusted under 35 U.S.C. 154(b) by 84 days.

This patent is subject to a terminal disclaimer.

(21) Appl. No.: 17/187,982

(22) Filed: Mar. 1, 2021

(65) Prior Publication Data

US 2021/0177721 A1    Jun. 17, 2021

Related U.S. Application Data

(63) Continuation of application No. 16/177,543, filed on Nov. 1, 2018, now Pat. No. 10,952,951, which is a continuation of application No. 15/586,362, filed on May 4, 2017, now abandoned, which is a continuation of application No. 14/105,230, filed on Dec. 13, 2013, now abandoned.

(60) Provisional application No. 61/879,217, filed on Sep. 18, 2013, provisional application No. 61/869,241, filed on Aug. 23, 2013, provisional application No. 61/737,257, filed on Dec. 14, 2012.

(51) Int. Cl.
| | |
|---|---|
| *A61K 8/49* | (2006.01) |
| *A61K 8/40* | (2006.01) |
| *A61Q 15/00* | (2006.01) |
| *A61K 8/46* | (2006.01) |
| *A61K 8/11* | (2006.01) |
| *A61L 9/01* | (2006.01) |
| *A61Q 5/02* | (2006.01) |
| *A61Q 13/00* | (2006.01) |
| *A61Q 19/00* | (2006.01) |
| *A61Q 19/10* | (2006.01) |
| *C11B 9/00* | (2006.01) |
| *C11D 3/50* | (2006.01) |
| *A61K 8/44* | (2006.01) |
| *A61K 8/28* | (2006.01) |
| *A61K 8/41* | (2006.01) |
| *A61K 8/60* | (2006.01) |
| *A61K 8/73* | (2006.01) |
| *C11D 3/00* | (2006.01) |
| *C11D 11/00* | (2006.01) |

(52) U.S. Cl.
CPC ............. *A61K 8/496* (2013.01); *A61K 8/11* (2013.01); *A61K 8/28* (2013.01); *A61K 8/40* (2013.01); *A61K 8/41* (2013.01); *A61K 8/445* (2013.01); *A61K 8/46* (2013.01); *A61K 8/49* (2013.01); *A61K 8/494* (2013.01); *A61K 8/4926* (2013.01); *A61K 8/4986* (2013.01); *A61K 8/602* (2013.01); *A61K 8/738* (2013.01); *A61L 9/01* (2013.01); *A61Q 5/02* (2013.01); *A61Q 13/00* (2013.01); *A61Q 15/00* (2013.01); *A61Q 19/00* (2013.01); *C11B 9/0011* (2013.01); *C11B 9/0023* (2013.01); *C11B 9/0084* (2013.01); *C11B 9/0092* (2013.01); *C11B 9/0096* (2013.01); *C11D 3/001* (2013.01); *C11D 3/502* (2013.01); *C11D 11/0017* (2013.01); *A61K 2800/56* (2013.01); *A61K 2800/77* (2013.01)

(58) Field of Classification Search
CPC .................................. A61K 8/46; C11D 3/50
See application file for complete search history.

(56) References Cited

U.S. PATENT DOCUMENTS

| | | |
|---|---|---|
| 3,328,402 A | 6/1967 | Max |
| 3,769,040 A | 10/1973 | Pittet |

(Continued)

FOREIGN PATENT DOCUMENTS

| | | |
|---|---|---|
| CN | 101040703 A | 9/2007 |
| CN | 101411458 A | 4/2009 |

(Continued)

OTHER PUBLICATIONS

"Antiperspirant and Breast Cancer Risk", American Cancer Society, 2008, 9 pages.

(Continued)

*Primary Examiner* — Mark V Stevens
(74) *Attorney, Agent, or Firm* — Andrew J. Mueller

(57) ABSTRACT

The present application relates to perfume raw materials, perfumes, perfume delivery systems and consumer products comprising such perfume raw materials, perfumes and/or such perfume delivery systems, as well as processes for making and using such perfume raw materials, perfume delivery systems and consumer products. The perfumes disclosed herein expand the perfume communities' options.

20 Claims, 1 Drawing Sheet

(56) References Cited

U.S. PATENT DOCUMENTS

| | | | |
|---|---|---|---|
| 3,899,597 A | 8/1975 | Mookherjee | |
| 3,900,558 A | 8/1975 | Kinsolving | |
| 3,917,870 A | 11/1975 | Slangan | |
| 3,928,248 A | 12/1975 | Mookherjee | |
| 4,031,034 A * | 6/1977 | Wilson | C11B 9/008 424/76.9 |
| 4,262,030 A | 4/1981 | Winter | |
| 4,324,703 A | 4/1982 | Seldner | |
| 4,430,243 A | 2/1984 | Bragg | |
| 4,478,865 A | 10/1984 | Demole | |
| 4,835,148 A | 5/1989 | Barford | |
| 4,869,875 A | 9/1989 | Skov | |
| 5,047,330 A | 9/1991 | Grassi | |
| 5,084,292 A | 1/1992 | Van Dort | |
| 5,252,604 A | 10/1993 | Nagy | |
| 5,262,153 A | 11/1993 | Mishima | |
| 5,278,048 A | 1/1994 | Parce | |
| 5,487,884 A | 1/1996 | Bissett | |
| 5,538,719 A | 7/1996 | Preti | |
| 5,574,179 A | 11/1996 | Wahl | |
| 5,576,282 A | 11/1996 | Miracle | |
| 5,597,936 A | 1/1997 | Perkins | |
| 5,651,976 A | 7/1997 | Price et al. | |
| 5,716,800 A | 2/1998 | Meybeck | |
| 5,861,144 A | 1/1999 | Peterson | |
| 5,866,142 A | 2/1999 | Riordan | |
| 5,890,489 A | 4/1999 | Elden | |
| 5,900,393 A | 5/1999 | Ramachandran | |
| 6,103,678 A | 8/2000 | Masschelein et al. | |
| 6,150,409 A | 11/2000 | Restrepo | |
| 6,184,188 B1 | 2/2001 | Severns | |
| 6,221,345 B1 | 4/2001 | Esser et al. | |
| 6,225,464 B1 | 5/2001 | Hiler, II | |
| 6,306,818 B1 | 10/2001 | Anderson | |
| 6,326,348 B1 | 12/2001 | Vinson | |
| 6,413,920 B1 | 7/2002 | Bettiol et al. | |
| 6,420,168 B1 | 7/2002 | Takeshita et al. | |
| 6,458,754 B1 | 10/2002 | Velazquez et al. | |
| 6,488,943 B1 | 12/2002 | Beerse et al. | |
| 6,517,819 B1 | 2/2003 | Breker | |
| 6,521,797 B1 | 2/2003 | Anderson | |
| 6,531,444 B1 | 3/2003 | Shefer et al. | |
| 6,734,158 B2 | 5/2004 | Starkenmann | |
| 7,018,978 B2 | 3/2006 | Miracle et al. | |
| 7,119,060 B2 | 10/2006 | Shefer et al. | |
| 7,192,913 B2 | 3/2007 | Clark et al. | |
| 7,223,361 B2 | 5/2007 | Kvietok | |
| 7,288,374 B2 | 10/2007 | Pincemail et al. | |
| 7,316,994 B2 | 1/2008 | Jordan, IV et al. | |
| 7,365,043 B2 | 4/2008 | Baker et al. | |
| 7,491,687 B2 | 2/2009 | Popplewell | |
| 7,585,833 B2 | 9/2009 | Fadel | |
| 7,590,232 B2 | 9/2009 | Carter et al. | |
| 7,722,807 B2 | 5/2010 | Keller, Jr. | |
| 7,761,242 B2 | 7/2010 | Honkonen et al. | |
| 7,763,238 B2 | 7/2010 | Preti | |
| 8,426,354 B2 | 4/2013 | Joichi | |
| 8,476,211 B2 | 7/2013 | Glenn, Jr. et al. | |
| 8,603,963 B1 | 12/2013 | Steward | |
| 8,651,395 B2 | 2/2014 | Kvietok et al. | |
| 8,754,028 B2 | 6/2014 | Velazquez | |
| 8,765,688 B2 | 7/2014 | Liebmann et al. | |
| 8,791,059 B2 | 7/2014 | Joichi | |
| 9,168,215 B2 | 10/2015 | Delattre et al. | |
| 9,499,770 B2 * | 11/2016 | Morgan, III | C11B 9/0092 |
| 9,708,568 B2 * | 7/2017 | Holland | C11B 9/0034 |
| 9,730,878 B2 | 8/2017 | Cetti et al. | |
| 9,949,911 B2 * | 4/2018 | Cetti | C11D 11/0017 |
| 10,568,825 B2 * | 2/2020 | Cetti | A61K 8/46 |
| 2003/0049220 A1 | 3/2003 | Bailey | |
| 2004/0110648 A1 | 6/2004 | Jordan, IV | |
| 2004/0110898 A1 | 6/2004 | Dreja | |
| 2004/0156742 A1 | 8/2004 | Milan | |
| 2005/0002894 A1 | 1/2005 | Petersohn | |
| 2005/0036972 A1 | 2/2005 | Cope | |
| 2005/0143282 A1 | 6/2005 | Creutz et al. | |
| 2005/0221334 A1 | 10/2005 | Benson | |
| 2005/0245407 A1 * | 11/2005 | Ishihara | A61Q 13/00 510/101 |
| 2005/0255077 A1 | 11/2005 | Golz-Berner et al. | |
| 2006/0003913 A1 | 1/2006 | Boutique et al. | |
| 2006/0115480 A1 | 6/2006 | Hillman | |
| 2006/0127996 A1 | 6/2006 | Fahey | |
| 2006/0257346 A1 | 11/2006 | Mohammadi et al. | |
| 2006/0263313 A1 | 11/2006 | Scavone | |
| 2007/0071780 A1 | 3/2007 | Dubois | |
| 2007/0178053 A1 | 8/2007 | Franklin | |
| 2007/0196344 A1 | 8/2007 | Osborne et al. | |
| 2007/0243625 A1 | 10/2007 | Oguri | |
| 2007/0275866 A1 | 11/2007 | Dykstra | |
| 2008/0014393 A1 * | 1/2008 | Denome | C11D 17/0039 428/35.7 |
| 2008/0138441 A1 | 6/2008 | Schwartz | |
| 2008/0200363 A1 | 8/2008 | Smets | |
| 2008/0265438 A1 | 10/2008 | Asano | |
| 2008/0305977 A1 | 12/2008 | Smets et al. | |
| 2009/0048365 A1 | 2/2009 | Brain | |
| 2009/0324660 A1 | 12/2009 | Cetti | |
| 2010/0028288 A1 | 2/2010 | Tranzeat et al. | |
| 2010/0233718 A1 | 9/2010 | Aubert et al. | |
| 2010/0267825 A1 | 10/2010 | Malfroy-Camine | |
| 2010/0287710 A1 | 11/2010 | Denutte et al. | |
| 2010/0297150 A1 | 11/2010 | Hillman | |
| 2010/0308130 A1 | 12/2010 | Gruenbacher | |
| 2011/0030095 A1 | 2/2011 | Favery | |
| 2011/0071123 A1 | 3/2011 | Schwartz et al. | |
| 2011/0086793 A1 | 4/2011 | Smets et al. | |
| 2011/0245141 A1 * | 10/2011 | Gizaw | C11D 3/3773 510/516 |
| 2011/0251872 A1 | 10/2011 | Wei | |
| 2011/0256071 A1 | 10/2011 | Blandino | |
| 2011/0262377 A1 | 10/2011 | Mckay | |
| 2011/0306538 A1 | 12/2011 | Joichi | |
| 2012/0020891 A1 | 1/2012 | Bares et al. | |
| 2012/0076839 A1 | 3/2012 | Chan | |
| 2012/0121677 A1 | 5/2012 | Franklin | |
| 2013/0005715 A1 | 1/2013 | Kobayakawa | |
| 2014/0170101 A1 | 6/2014 | Cetti | |
| 2014/0170102 A1 | 6/2014 | Cetti et al. | |
| 2014/0170194 A1 | 6/2014 | Cetti et al. | |
| 2014/0179722 A1 | 6/2014 | Cetti | |
| 2014/0179748 A1 | 6/2014 | Cetti et al. | |
| 2014/0271930 A1 | 9/2014 | Kerr et al. | |
| 2014/0273055 A1 | 9/2014 | Kerr et al. | |
| 2015/0164764 A1 | 6/2015 | Bonnet et al. | |
| 2015/0322376 A1 | 11/2015 | Holland | |
| 2017/0233679 A1 | 8/2017 | Cetti | |
| 2017/0267944 A1 | 9/2017 | Holland | |
| 2017/0312204 A1 | 11/2017 | Cetti | |
| 2018/0064588 A1 | 3/2018 | Sturgis | |
| 2018/0207074 A1 | 7/2018 | Cetti | |
| 2019/0070086 A1 | 3/2019 | Cetti | |
| 2020/0146960 A1 | 5/2020 | Cetti | |

FOREIGN PATENT DOCUMENTS

| | | | |
|---|---|---|---|
| EP | 0483426 A1 | 5/1992 | |
| EP | 0816322 A1 | 1/1998 | |
| EP | 0980863 A1 | 2/2000 | |
| EP | 2263700 A1 | 12/2010 | |
| FR | 2338037 A1 | 8/1977 | |
| JP | S5754133 A | 3/1982 | |
| JP | S6157510 A | 3/1986 | |
| JP | H0240370 A | 2/1990 | |
| JP | H04255796 A | 9/1992 | |
| JP | 2004231543 A | 8/2004 | |
| JP | 2005015683 A | 1/2005 | |
| JP | 3649441 B1 | 2/2005 | |
| JP | 2005170811 A | 6/2005 | |
| JP | 2006025706 A | 2/2006 | |
| JP | 2008050464 A | 3/2008 | |
| JP | 2008154476 A | 7/2008 | |
| JP | 2008297355 | 12/2008 | |
| JP | 2009023964 A | 2/2009 | |

(56) References Cited

FOREIGN PATENT DOCUMENTS

| | | |
|---|---|---|
| JP | 2010202618 A | 9/2010 |
| JP | 2011068836 A | 4/2011 |
| JP | 2012219012 A | 11/2012 |
| JP | 2013006967 A | 1/2013 |
| KR | 101022321 B1 | 3/2011 |
| WO | 9629281 A1 | 9/1996 |
| WO | 02098966 A2 | 12/2002 |
| WO | 2008149065 A1 | 12/2008 |
| WO | 2008151273 A2 | 12/2008 |
| WO | 2009131748 A1 | 10/2009 |
| WO | 2010031657 A2 | 3/2010 |
| WO | 2010094546 A2 | 8/2010 |
| WO | 2011096575 A1 | 8/2011 |

OTHER PUBLICATIONS

"Standard Practice for Determination of Odor and Taste Thresholds by a Forced-Choice Ascending Concentration Series Method of Limits", ASTM International, Designation: E679-04 (Reap proved 2011), pp. 1-7.
All Office Actions, U.S. Appl. No. 14/105,230.
All Office Actions, U.S. Appl. No. 15/586,362.
All Office Actions, U.S. Appl. No. 16/177,543.
All Office Actions; U.S. Appl. No. 11/655,347.
All Office Actions; U.S. Appl. No. 12/562,757.
All Office Actions; U.S. Appl. No. 14/105,549.
All Office Actions; U.S. Appl. No. 14/211,767.
All Office Actions; U.S. Appl. No. 16/747,612.
Aubert, J. et al. "Gene Expression Profiling in Psoriatic Scalp Hair Follicles: Clobetason Propionate Shampoo 0.05% normalizes Psoriasis Disease Markers" J. European Academy of Dermatology and Venereology, vol. 24, Issue 11, pp. 1304-1311.
Baek, J. et al: "Assessment of an imiquimod-induced psoriatic mouse model in relation to oxidative stress", Archives of Dermatological Research ; vol. 304, No. 9, Aug. 5, 2012 (Aug. 5, 2012), pp. 699-706.
Balaskas, E. et al., "Histamine and Serotonin as Markers of Uremic Pruritus", Clinical Chemistry, vol. 43, No. 6, Part 2, 1997; p. S113.
Dalton et al., "The Nature and Duration of Adaptation Following Long-Term Odor Exposure", Percept Psychophysics, vol. 58, No. 5, Jul. 1996, pp. 781-792.
E.M. Martin Del Valle "Cyclodextrins and their uses: a review" Department of Chemical Engineering, University of Salamanca, 2003, pp. 1-14.
Eckert, R. L. et al. "S100 Proteins in the Epidermis" J. Investigative Dermatology (2004), 123 (1), 23-33.
Emre, S. et al."The association of oxidative stress and disease activity in seborrheic dermatitis" Arch Dermatol. Res (2012) 304:683-687.
Fortineau "Chemistry Perfumes your daily life". Journal of Chemical Education, vol. 81, No. 01, Jan. 2004, pp. 45-50.
Glaeser Regine et al: "Antimicrobial psoriasin (SI00A7) protects human skin from *Escherichia coli* infection". Nature Immunology. Nature Publishing Group. GB. vol. 6. No. 1. Jan. 1, 2005 (Jan. 1, 2005) pp. 57-64.
Goodscents Company "Dibutyl_Sulfide" pp. 1-15.
International Search Report and Written Opinion; Application Ser. No. PCT/US2010/048185; dated Dec. 22, 2010, 11 pages.
International Search Report and Written Opinion; Application Ser. No. PCT/US2013/074886; dated Jun. 4, 2014, 26 pages.
International Search Report and Written Opinion; Application Ser. No. PCT/US2013/074986; dated May 19, 2014; 13 pages.
International Search Report and Written Opinion; Application Ser. No. PCT/US2014/028537; dated Nov. 17, 2014, 16 pages.
International Search Report and Written Opinion; Application Ser. No. PCT/US2014/028598; dated Jul. 15, 2014, 11 pages.
International Search Report and Written Opinion; Application Ser. No. PCT/US2014/028631; dated Jan. 5, 2015, 16 pages.
M. Iranshahi_"A review of volatile sulfur-containing compounds from terrestrial plants: biosynthesis, distribution and analytical met hods", Journal of Essential Oil Research, Aug. 2012, vol. 24, No. 04, pp. 393-434.
St. Croix Sensory, Inc. "A Review of the Science and Technology of Odor Measurement" Prepared for Air Quality Bureau of the Iowa Department of Natural Resources. Dec. 30, 2005, 51 pages.
Y. Ashida et al., "Dry Environment Increases Mast Cell Number and Histamine Content in Dermis in Hairless Mice", British Journal of Dermatology 2003; 149; 240-247.
"2-Methyl-3-(methylthio)pyrazine", URL Link: https://pubchem.ncbi.nlm.nih.gov/compound/76152 dated Aug. 27, 2022, 52 Pages.

\* cited by examiner

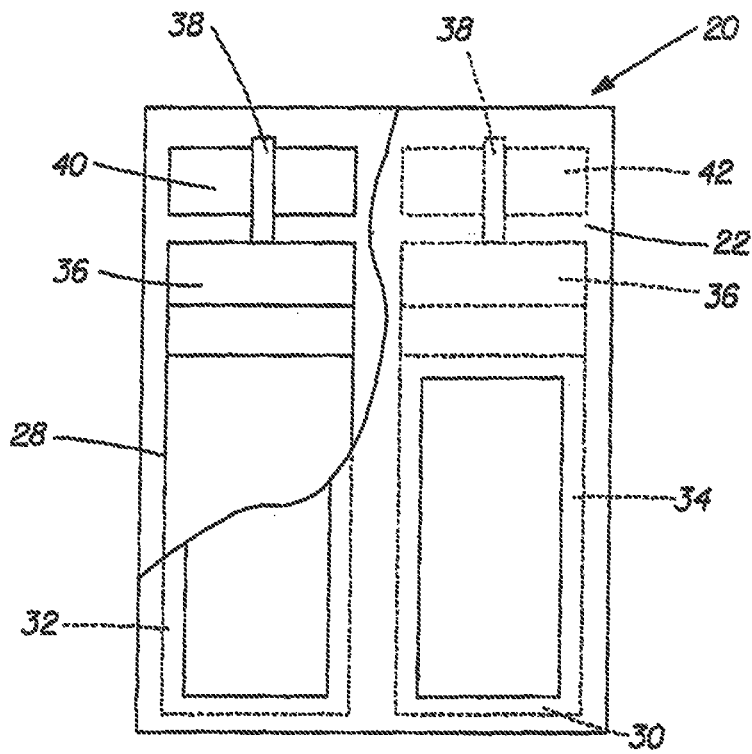
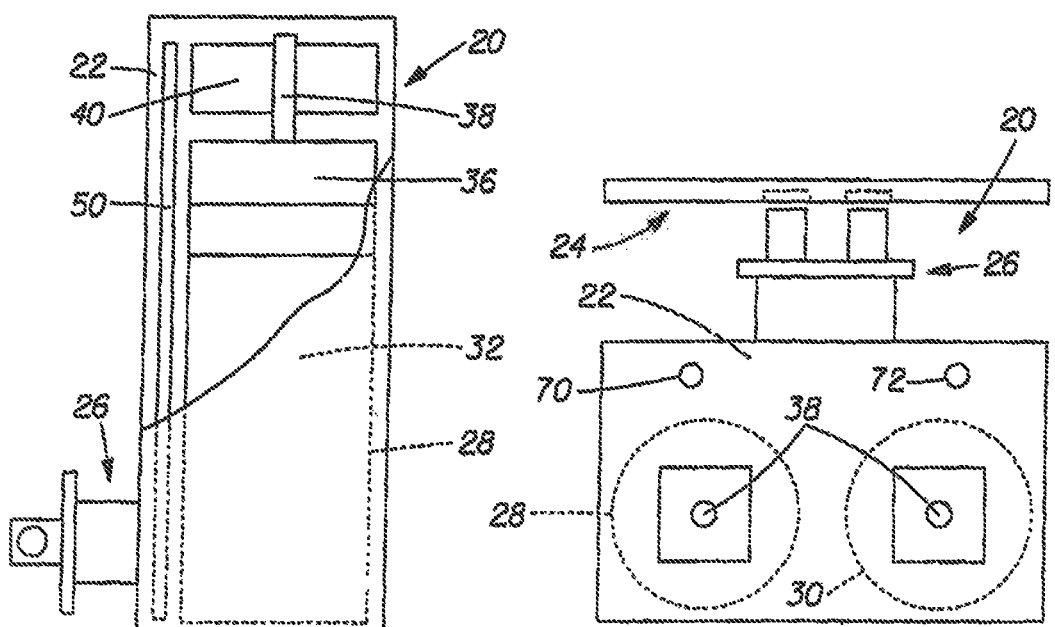

FRAGRANCE MATERIALS

FIELD OF INVENTION

The present application relates to perfume raw materials, perfumes, perfume delivery systems and consumer products comprising such perfume raw materials, perfumes and/or such perfume delivery systems, as well as processes for making and using such perfume raw materials, perfumes, perfume delivery systems and consumer products.

BACKGROUND OF THE INVENTION

Consumer products may comprise one or more perfumes and/or perfume delivery systems that can provide a desired scent to such product and/or a situs that is contacted with such a product and/or mask an undesirable odor. While current perfumes and perfume delivery systems provide desirable odors, consumers continue to seek products that have scents that may be longer lasting and that are tailored to their individual desires—unfortunately consumers become habituated to perfume raw materials (PRMs) and perfumes. As a result, ever increasing amounts of such PRMs and/or perfumes are required to achieve the same effect or the consumer must switch to a different product and/or perfume for a significant period of time to reverse such habituation.

While not being bound by theory, Applicants believe that habituation is a phenomenon that is grounded in the consumer's physiology, in that the body is attempting to avoid having its sense smell from being overwhelmed by any one stimulus after repeated chronic exposure of said stimulus. This defense mechanism is likely a primal, darwanistic defense mechanism. In short, Applicants recognized that the source of habituation problem likely laid in evolution. As a result, Applicants looked to odors that may be associated with danger as Applicants believed that the evolutionary path of those who became habituated to such odors would have been cut short. Surprisingly, Applicants found that certain chemical moieties that are associated with conditions that may be detrimental to or important in sustaining life, are not subject to the habituation phenomenon. Based on this recognition, Applicants identified perfume raw materials, and developed perfumes, perfume delivery systems and consumer products comprising such perfume raw materials, perfumes and/or such perfume delivery systems, as well as processes for making and using such perfume raw materials, perfume delivery systems and consumer products that are not as susceptible to habituation.

SUMMARY OF THE INVENTION

The present application relates to perfume raw materials, perfumes, perfume delivery systems and consumer products comprising such perfume raw materials, perfumes and/or such perfume delivery systems, as well as processes for making and using such perfume raw materials, perfume delivery systems and consumer products.

BRIEF DESCRIPTION OF THE DRAWINGS

It is believed that at least one aspect of the present invention will be better understood from the following description taken in conjunction with the accompanying drawings in which:

FIG. 1 is a partially fragmented schematic front view showing one non-limiting embodiment of a device for emitting volatile compositions.

FIG. 2 is a partially fragmented schematic side view of the device shown in FIG. 1.

FIG. 3 is a schematic top view of the device shown in FIG. 1, showing the same adjacent to the cover plate of an electrical outlet.

DETAILED DESCRIPTION OF THE INVENTION

Definitions

As used herein "consumer product" means baby care, beauty care, fabric & home care, family care, feminine care, health care, snack and/or beverage products, packaging or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

As used herein, the term "neat" when used in the context of a perfume, means the perfume is not part of/contained in a perfume delivery system.

The perfume raw materials disclosed, claimed and/or used in the perfumes claimed and/or described herein encompass any stereoisomers of such perfume raw materials.

As used herein, the term "habituating" refers an individual or group who has decreased sensitivity to perceiving a fragrance or fragrance material. A fragrance or fragrance material is considered habituating when their Degree of Habituation (percent change in ODT) is greater than 150%, greater than 300%, greater than 500%, greater than 1000% according to the method described in the Test Methods section of this specification.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfumes

In one aspect, a perfume comprising, based on total perfume weight, a perfume raw material selected from the group consisting of:
a) from about 0.0000001% to about 10%, from about 0.000001% to about 5%, from about 0.000005% to about 2.5%, from about 0.00001% to about 1%, from about 0.000025% to about 0.8%, of a perfume raw material comprising a thiol moiety;
b) from about 0.0000001% to about 10%, from about 0.0000001% to about 5%, from about 0.000005% to about 2.5%, from about 0.00001% to about 1%, from about 0.000025% to about 0.5%, of a perfume raw material comprising a sulfide moiety;
c) from about 0.000001% to about 10%, from about 0.000005% to about 5%, from about 0.00001% to about 2.5%, from about 0.0005% to about 1%, from about 0.001% to about 0.1%, of a perfume raw material comprising a thiazole moiety;
d) from about 0.00000005% to about 5%, from about 0.0000001% to about 2.5%, from about 0.0000005% to about 2%, from about 0.000001% to about 1%, from about 0.000005% to about 0.5%, of a perfume raw material comprising a pyrazine moiety;
e) from about 0.00001% to about 20%, from about 0.0001% to about 15%, from about 0.001% to about 10%, from about 0.01% to about 5%, from about 0.1% to about 2.5%, of a perfume raw material comprising a nitrile moiety;
f) from about 0.000001% to about 10%, from about 0.00001% to about 7%, from about 0.0001% to about 4%, from about 0.001% to about 2%, from about 0.01% to about 1%, of a perfume raw material comprising an indole moiety;
g) from about 0.0000001% to about 10%, from about 0.000001% to about 5%, from about 0.000005% to about 2.5%, from about 0.00001% to about 1%, from about 0.000025% to about 0.8%, of a perfume raw material comprising an oxathiane moiety;
h) from about 0.00001% to about 10%, from about 0.0001% to about 7.5%, from about 0.001% to about 5%, from about 0.005% to about 2.5%, from about 0.01% to about 1%, of a perfume raw material comprising an oxime moiety;
i) from about 0.00001% to about 20%, from about 0.0001% to about 15%, from about 0.001% to about 10%, from about 0.01% to about 5%, from about 0.1% to about 2.5%, of a perfume raw material comprising an amine moiety;
j) from about 0.00000005% to about 5%, from about 0.0000001% to about 2.5%, from about 0.0000005% to about 2%, from about 0.000001% to about 1%, from about 0.000005% to about 0.5%, of a perfume raw material comprising an isothiocyanate;
k) from about 0.00000005% to about 5%, from about 0.0000001% to about 2.5%, from about 0.0000005% to about 2%, from about 0.000001% to about 1%, from about 0.000005% to about 0.5%, of a perfume raw material comprising a diamine moiety;
l) from about 0.000001% to about 10%, from about 0.000005% to about 5%, from about 0.00001% to about 2.5%, from about 0.0005% to about 1%, from about 0.001% to about 0.1%, of a perfume raw material comprising oxygen, sulfur, and nitrogen; and
m) mixtures thereof, with the proviso that the sum of the percentage of said perfume raw materials cannot exceed 100%, is disclosed.

In one aspect, said perfume comprises, based on total perfume weight, a perfume raw material selected from the group consisting of: items a), b) c), d), g), h), j), k), l), m) and mixtures thereof.

In one aspect, said perfume comprises, based on total perfume weight, a perfume raw material selected from the group consisting of: items a), b) c), d), g), m) and mixtures thereof.

In one aspect, of said perfume:
a) said perfume raw material comprising a thiol moiety is selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; Ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl) prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl) propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo[3.1.1]heptanyl)methanethiol; methyldisulfanylbenzene; 1-butyldisulfanylbutane; (4-methoxyphenyl) methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; 2-methyl-2-sulfanylpentan-1-ol; and mixtures thereof;
b) said perfume raw material comprising a sulfide moiety is selected from the group consisting of 1-butylsulfanylbutane; ethyl 3-methylsulfanylpropanoate; 2-(methylsulfanylmethyl)furan; methyl sulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methyl sulfanylbutane; 2-propan-2-ylsulfanylpropane; bis(methylsulfanyl)methane; 1-ethyl sulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enylpropanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl3-methylbutanethioate; 4-methyl-4-methylsulfanylpentan-2-one; 2-methyl-1,3-dithiolane; methyl 2-methylsulfanylbutanoate; S-methylfuran-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl) methanethioate; 1,2,4-trithiolane; 2-methylthiolan-3-one; 4-methylsulfanylbutan-1-ol; S-butan-2-yl3-methylbutanethioate; S-butan-2-yl3-methylbut-2-enethioate; S-(furan-2-ylmethyl) ethanethioate; 2-propyl-1,3-thiazolidine; 1-bis(methylsulfanyl)butane; 3-ethylsulfanylpropan-1-ol; S-methyl benzenecarbothioate; 3,5-dimethyl-1,2,4-trithiolane; S-butan-2-yl2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl) ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methyl sulfanylpyrazine; 2-(furan-2-ylmethylsulfanylmethyl)furan; 2-(methylsulfanylmethyl)pyrazine; 3,5-di(propan-2- yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate and mixtures thereof;
c) said perfume raw material comprising a thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; 4-methyl-2-propan-2-yl-1,3-thiazole; and mixtures thereof;
d) said perfume raw material comprising a pyrazine moiety is selected from the group consisting of 2-methoxy-3-(2-methylpropyl)pyrazine; 2,3-dimethylpyrazine; 1-pyrazin-2-ylethanone; 2-methyl-3-methylsulfanylpyrazine; Pyrazine; 2-methylpyrazine; 2-ethenylpyrazine; 2-ethylpyrazine; 2,6-dimethylpyrazine; 2,5-dimethylpyrazine; 2-prop-1-en-2-ylpyrazine; 2-propan-2-ylpyrazine; 2-methoxypyrazine; 2-ethenyl-5-methylpyrazine; 2-ethyl-5-methylpyrazine; 2-Ethyl-6-methylpyrazine; 2-Ethyl-3-Methyl-Pyrazine; 2-propylpyrazine; 2,3,5-trimethylpyrazine; 2-tert-butylpyrazine; pyrazin-2-amine; 2-(2-methylpropyl)pyrazine; 2-methyl-5-propan-2-ylpyrazine; 2-(methoxymethyl)pyrazine; 2,3-diethylpyrazine; 2-ethyl-3,(5 OR 6)-dimethylpyrazine; 2-ethyl-3,5-dimethylpyrazine; 2-ethyl-2,5-dimethylpyrazine; 3-ethyl-2,5-dimethylpyrazine; 2-ethyl-3,5-dimethylpyrazine; 2-methyl-3-propylpyrazine; 2,3,5,6-tetramethylpyrazine; 7-methyl-6,7-dihydro-5H-cyclopenta[b]pyrazine; 2-methylsulfanylpyrazine; 2-methyl-3-methylsulfanylpyrazine; 2-ethoxy-3-ethylpyrazine; 2-Isobutyl-3-methylpyrazine; pyrazin-2-ylmethanethiol; 3,5-dimethyl-2-propylpyrazine; 2-ethyl-3-methoxypyrazine; 2-ethoxy-3-methylpyrazine; 2-ethyl-5-methoxypyrazine; 5,6,7,8-tetrahydroquinoxaline; 2-ethoxy-3-propan-2-ylpyrazine; 2-(methylsulfanylmethyl)pyrazine; 3,5-dimethyl-2-(2-methylpropyl)pyrazine; 2,3-diethyl-5-methylpyrazine; 3,5-Diethyl-2-methylpyrazine; 2,5-dimethyl-3-(2-methylpropyl)pyrazine; 2-methyl-6-propoxypyrazine; 2-(2-methylpropoxy)pyrazine; 1-(3-methylpyrazin-2-yl)ethanone; 2-methyl-3-methylsulfanylpyrazine; 2-methoxy-3-propan-2-ylpyrazine; quinoxaline; 3-butyl-2,5-dimethylpyrazine; 2-butyl-3,5-dimethylpyrazine; 2-pyrazin-2-ylethanethiol; 1-(3-ethylpyrazin-2-yl)ethanone; 1-(3,5-dimethylpyrazin-2-yl)ethanone; 2-butan-2-yl-3-methoxypyrazine; 2-methylquinoxaline; 5-Methylquinoxaline; 2-methoxy-3-(4-methylpentyl)pyrazine; 2,3-dimethylquinoxaline; 2-(cyclohexylmethyl)pyrazine; 2-[(furan-2-ylmethyl)sulfanyl]-5-methylpyrazine and mixtures thereof;
e) said perfume raw material comprising a nitrile moiety is selected from the group consisting of 3,7-dimethyl-oct-6-enenitrile, 3-(4-ethylphenyl)-2,2-dimethylpropanenitrile; and mixtures thereof;
f) said perfume raw material comprising a indole moiety is selected from the group consisting of 1H-indole, 3-methyl-1H-indole; and mixtures thereof;
g) said perfume raw material comprising a oxathiane moiety is selected from the group consisting of (2R, 4S)-2-methyl-4-propyl-1,3-oxathiane, 2-methyl-4-propyl-1,3-oxathiane, 2-pentyl-4-propyl-1,3-oxathiane; and mixtures thereof;
h) said perfume raw material comprising a oxime moiety is selected from the group consisting of (NE)-N-[(6E)-2,4,4,7-tetramethylnona-6,8-dien-3-ylidene]hydroxylamine, N-(5-methylheptan-3-ylidene)hydroxylamine, and mixtures thereof;
i) said perfume raw material comprising an amine moiety is selected from the group consisting of methyl 2-aminobenzoate, pentane-1,5-diamine; 6-methyl-7-Oxa-1-thia-4-azaspiro[4.4]nonane; and mixtures thereof;

In one aspect of said perfume, said perfume raw material comprises at least one sulfur, oxygen and nitrogen atom, said perfume raw material being selected from the group consisting of 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methyl sulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid; and mixtures thereof.

In one aspect of said perfume:
a) said perfume raw material comprises a thiol moiety is selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; and mixtures thereof;
b) said perfume raw material comprises a sulfide moiety is selected from the group consisting of 1-butylsulfanylbutane; ethyl 3-methylsulfanylpropanoate; 2-(methylsulfanylmethyl)furan; and mixtures thereof;
c) said perfume raw material comprises a thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; 1-(1,3-thiazol-2-yl)ethanone; and mixtures thereof;
d) said perfume raw material comprises a pyrazine moiety is selected from the group consisting of 2-methoxy-3-(2-methylpropyl)pyrazine; 2,3-dimethylpyrazine; 1-pyrazin-2-ylethanone; 2-methyl-3-methylsulfanylpyrazine; and mixtures thereof;
e) said perfume raw material comprises a nitrile moiety is selected from the group consisting of 3,7-dimethyloct-6-enenitrile, 3-(4-ethylphenyl)-2,2-dimethylpropanenitrile; and mixtures thereof;
f) said perfume raw material comprises a indole moiety is selected from the group consisting of 1H-indole.

g) said perfume raw material comprises a oxathiane moiety is selected from the group consisting of (2R, 4S)-2-methyl-4-propyl-1,3-oxathiane.
h) said perfume raw material comprises a oxime moiety is selected from the group consisting of (NE)-N-[(6E)-2, 4,4,7-tetramethylnona-6,8-dien-3-ylidene]hydroxylamine.
i) said perfume raw material comprises a amine moiety is selected from the group consisting of methyl 2-aminobenzoate, pentane-1,5-diamine, 6-methyl-7-Oxa-1-thia-4-azaspiro[4.4]nonane; and mixtures thereof;
j) said perfume raw material comprises oxygen, sulfur, and nitrogen is selected from the group consisting of 2-(4-methyl-1,3-thiazol-5-yl)ethanol, 1-(1,3-thiazol-2-yl)ethanone; 6-methyl-7-Oxa-1-thia-4-azaspiro[4.4]nonane; and mixtures thereof.

In one aspect of said perfume, said perfume raw material comprises a perfume raw material selected from the group consisting of:
a) 1-butylsulfanylbutane; (2R,4S)-2-methyl-4-propyl-1,3-oxathiane; and 4-methoxy-2-methylbutane-2-thiol;
b) (NE)-N-[(6E)-2,4,4,7-tetramethylnona-6,8-dien-3-ylidene]hydroxylamine; and 7-hydroxy-3,7-dimethyloctanal; 3-(4-ethylphenyl)-2,2-dimethylpropanenitrile;
c) 2-(4-methyl-1,3-thiazol-5-yl)ethanol; 7-Oxa-1-thia-4-azaspiro[4.4]nonane; and 6-methyl-, 1-(1,3-thiazol-2-yl)ethanone;
d) 2-methoxy-3-(2-methylpropyl)pyrazine; 1-pyrazin-2-ylethanone; and 2,3-dimethylpyrazine;
e) 2-(methylsulfanylmethyl)furan; ethyl 3-methyl sulfanylpropanoate; and 1-butylsulfanylbutane;
f) 5-methyl-5-sulfanylhexan-3-one; 5-methyl-2-(2-sulfanylpropan-2-yl)cyclohexan-1-one; and 2-(4-methyl-1-cyclohex-3-enyl)propane-2-thiol;
g) 2-methoxy-3-(2-methylpropyl)pyrazine; 3,7-dimethyloct-6-enenitrile; and methyl 2-aminobenzoate;
h) 2-(2-methylpropyl)-1,3-thiazole; 2-(4-methyl-1,3-thiazol-5-yl)ethanol; and 4-methyl-2-propan-2-yl-1,3-thiazole;
i) (2R,4S)-2-methyl-4-propyl-1,3-oxathiane; 2-(4-methyl-1-cyclohex-3-enyl)propane-2-thiol; and (NE)-N-[(6E)-2,4,4,7-tetramethylnona-6,8-dien-3-ylidene]hydroxylamine; and
j) mixtures thereof.

In one aspect of said perfume composition, said composition comprises a perfume raw material selected from the group consisting of:
a) a perfume raw material comprising a sulfide moiety, in one aspect, said perfume raw material comprising a sulfide moiety is selected from the group consisting of 1-butylsulfanylbutane, 4,7,7-trimethyl-6-thiabicyclo[3.2.1]octane, and 2-methyl-3-methyl sulfanylpyrazine and mixtures thereof;
b) a perfume raw material comprising a thiazole moiety, in one aspect, said material comprising a thiazole moiety is selected from the group consisting of 1-(1,3-thiazol-2-yl)ethanone;
c) a perfume raw material comprising a pyrazine moiety and acetyl moiety, in one aspect, said material comprising a pyrazine moiety and acetyl moiety is selected from the group consisting of 1-pyrazin-2-ylethanone;
d) a perfume raw material comprising an oxime moiety, in one aspect, said material comprising an oxime moiety is selected from the group consisting of (NE)-N-[(6E)-2,4,4,7-tetramethylnona-6,8-dien-3-ylidene]hydroxylamine; and
e) mixtures thereof.

In one aspect, a perfume having:
a) a two week anti-habituation index of at least 0, 1, 2, 3 or 4;
b) a four week anti-habituation index of at least 0, 1, 2, 3, or 4;
c) a two week anti-habituation index of 0, 1, 2, 3 or 4; and/or
d) a four week anti-habituation index of 0, 1, 2, 3 or 4 is disclosed.

In one aspect, said perfume composition may contain a fragrance modulator. Fragrance modulators enhance intensity of a fragrance profile over time, preferably so that the volatile fragrance materials remain significantly consistent from its initial impression to the end. Fragrance modulators are disclosed in U.S. Provisional Patent Ser. No. 61/915,514 which is incorporated by reference. Thus, in one aspect, said perfume composition comprises:
a) a fragrance component present in an amount of from about 1 wt % to about 30 wt %, preferably less than about 20 wt %, preferably less than about 15 wt %, preferably less than about 10 wt % or preferably less than 8 wt %, relative to the total weight of the composition; and wherein:
  (i) the fragrance component comprises at least one low volatile fragrance material having a vapor pressure less than 0.001 Torr; and
  (ii) the low volatile fragrance material is present in an amount of from about 0.1 wt % to about 30 wt %, preferably less than about 25 wt %, preferably less than about 20 wt %, or preferably less than about 12 wt %, relative to the total weight of the fragrance component;
b) at least one non-odorous fragrance modulator formed of an alkoxylated methyl glucoside selected from the group consisting of methyl glucoside polyol, ethyl glucoside polyol, and propyl glucoside polyol, preferably PPG-20 Methyl Glucose Ether, in an amount of from about 0.1 wt % to about 20 wt %, preferably about 0.5 wt % to ab out 18 wt %, or more preferably about 2.5 wt % to about 15%, relative to the total weight of the composition.

In one aspect, said low volatile fragrance material is selected from the group consisting of: 2-Buten-1-ol, 2-methyl-4-(2,2,3-trimethyl-3-cyclopenten-1-yl)-; Ethanone, 1-(2-naphthalenyl)-; 3-Decanone, 1-hydroxy-; Cyclopropanemethanol, 1-methyl-2-[(1,2,2-trimethylbicyclo[3.1.0]hex-3-yl)methyl]-; Benzaldehyde, 3-ethoxy-4-hydroxy-; 2H-1,5-Benzodioxepin-3(4H)-one, 7-methyl-; 2-Butanol, 1-[[2-(1,1-dimethylethyl)cyclohexyl]oxy]-; Spiro[5.5]undec-8-en-1-one, 2,2,7,9-tetramethyl-; Cyclopentaneacetic acid, 3-oxo-2-pentyl-, methyl ester, (1R,2R)-rel-; Cyclopentaneacetic acid, 3-oxo-2-pentyl-, methyl ester; Octanal, 2-(phenylmethylene)-; Indeno [4,5-d]-1,3-dioxin, 4,4a,5,6,7,8,9,9b-octahydro-7,7,8,9,9-pentamethyl-; Cyclopentanecarboxylic acid, 2-hexyl-3-oxo-, methyl ester; 3-Cyclopentene-1-butanol, α,β,2,2,3-pentamethyl-; Cyclopentanone, 2-(3,7-dimethyl-2,6-octadien-1-yl)-; 1,6,10-Dodecatrien-3-ol, 3,7,11-trimethyl-; 2-Pentenenitrile, 3-methyl-5-phenyl-, (2Z)-; Benzenepropanenitrile, 4-ethyl-α,α-dimethyl-; 1H-3a,7-Methanoazulen-6-ol, octahydro-3,6,8,8-tetramethyl-, (3R,3a S,6R,7R,8a S)-; Ethanone, 1-(1,2,3,5,6,7,8,8a-octahydro-2,3,8,8-tetramethyl-2-naphthalenyl)-; Ethanone, 1-(1,2,3,4,5,6,7,8-octahydro-2,3,8,8-tetramethyl-2-naphthalenyl)-; Propanoic acid, 2-methyl-, 4-formyl-2-methoxyphenyl ester; 1,6-Heptadien-3-one, 1-(2,6,6-trimethyl-2-cyclohexen-1-yl)-; Benzoic acid, 2-hydroxy-, hexyl ester; Benzoic acid, phenyl ester;

Cyclohexanepropanol, 2,2,6-trimethyl-α-propyl-, (1R,6S)-; Cyclohexanepropanol, 2,2,6-trimethyl-α-propyl-; Benzoic acid, 2-hydroxy-, 3-methyl-2-buten-1-yl ester; 2H-1,5-Benzodioxepin-3(4H)-one, 7-(1-methylethyl)-; Butanal, 4-(octahydro-4,7-methano-5H-inden-5-ylidene)-; Cyclopenta[g]-2-benzopyran, 1,3,4,6,7,8-hexahydro-4,6,6,7,8,8-hexamethyl-; Cyclopentanone, 2-[2-(4-methyl-3-cyclohexen-1-yl)propyl]-; 2(3H)-Naphthalenone, 4,4a,5,6,7,8-hexahydro-4,4a-dimethyl-6-(1-methylethenyl)-, (4R,4aS,6R)-; 2-Propenoic acid, 3-phenyl-, pentyl ester; 4H-Pyran-4-one, 3-hydroxy-2-methyl-; 1-Propanol, 2-methyl-3-[(1,7,7-trimethylbicyclo[2.2.1]hept-2-yl)oxy]-; 1-Naphthalenol, 1,2,3,4,4a,5,8,8a-octahydro-2,2,6,8-tetramethyl-; 2-Butenoic acid, 2-methyl-, (2E)-3,7-dimethyl-2,6-octadien-1-yl ester, (2E)-; 1,3-Dioxane, 2-(2,4-dimethyl-3-cyclohexen-1-yl)-5-methyl-5-(1-methylpropyl)-; 4-Penten-2-ol, 3-methyl-5-(2,2,3-trimethyl-3-cyclopenten-1-yl)-; Propanoic acid, 2-methyl-, 2-methyl-4-oxo-4H-pyran-3-yl ester; 2-Buten-1-ol, 2-ethyl-4-(2,2,3-trimethyl-3-cyclopenten-1-yl)-; 1,6-Methanonaphthalen-1(2H)-ol, octahydro-4,8a,9,9-tetramethyl-, (1R,4S,4aS,6R,8aS)-; 2H-1,5-Benzodioxepin-3(4H)-one, 7-(1,1-dimethylethyl)-; Benzoic acid, phenylmethyl ester; 8-Cyclohexadecen-1-one; Benzoic acid, 2-hydroxy-, (3Z)-3-hexen-1-yl ester; 4H-Pyran-4-one, 2-ethyl-3-hydroxy-; Cyclopentadecanone, 3-methyl-; Benzoic acid, 2-hydroxy-, phenylmethyl ester; 6,8-Nonadien-3-one, 2,4,4,7-tetramethyl-, oxime; Benzoic acid, 2-hydroxy-, cyclohexyl ester; Benzene, [2-(dimethoxymethyl)-1-hepten-1-yl]-; 3-Cyclopentene-1-butanol, (3,2,2,3-tetramethyl-6-methylene-; 4-Penten-1-one, 1-spiro[4.5]dec-7-en-7-yl-; Acetic acid, 2-(1-oxopropoxy)-, 1-(3,3-dimethylcyclohexyl) ethyl ester; 4-Penten-2-ol, 3,3-dimethyl-5-(2,2,3-trimethyl-3-cyclopenten-1-yl)-; 5,8-Methano-2H-1-benzopyran-2-one, 6-ethylideneoctahydro-; 4-Cyclopentadecen-1-one, (4Z)-; Ethanone, 1-[(3R,3aR,7R,8aS)-2,3,4,7,8,8a-hexahydro-3,6,8,8-tetramethyl-1H-3a,7-methanoazulen-5-yl]-; 1,3-Dioxolane, 2,4-dimethyl-2-(5,6,7,8-tetrahydro-5,5,8,8-tetramethyl-2-naphthalenyl)-; Oxacyclohexadecan-2-one; 1-Propanol, 2-[1-(3,3-dimethylcyclohexyl)ethoxy]-2-methyl-, 1-propanoate; 5-Cyclopentadecen-1-one,3-methyl-; 2H-1,5-Benzodioxepin-3 (4H)-one, 7-(3-methylbutyl)-; Ethanone, 1-(2,6,10-trimethyl-2,5,9-cyclododecatrien-1-yl)-; 1H-3a,6-Methanoazulene-3-methanol, octahydro-7,7-dimethyl-8-methylene-, (3S,3aR,6R,8aS)-; Benzeneacetonitrile, α-cyclohexylidene-; Benzoic acid, 2-[(2-methylpentylidene)amino]-, methyl ester; Benzoic acid, 2-phenylethyl ester; Cyclohexanol, 4-(1,7,7-trimethylbicyclo[2.2.1]hept-2-yl)-; 3-Cyclohexene-1-carboxaldehyde, 4-(4-hydroxy-4-methylpentyl)-; Ethanone, 1-(5,6,7,8-tetrahydro-3,5,5,6,8,8-hexamethyl-2-; 2-Cyclopentadecen-1-one, 3-methyl-; Oxacycloheptadecan-2-one; Benzeneacetic acid, 4-methylphenyl ester; Benzeneacetic acid, 2-phenylethyl ester; Cyclododecaneethanol, 3-methyl-; 2-Propenoic acid, 3-phenyl-, phenylmethyl ester; Benzoic acid, 2,4-dihydroxy-3,6-dimethyl-, methyl ester; Naphtho[2,1-b]furan-6(7H)-one, 8,9-dihydro-1,5,8-trimethyl-, (8R)-; Benzeneacetic acid, (4-methoxyphenyl) methyl ester; Benzene, 2-methoxy-1-(phenylmethoxy)-4-(1-propen-1-yl)-; Benzeneacetic acid, (2E)-3,7-dimethyl-2,6-octadien-1-yl ester; Benzoic acid, 2-hydroxy-, 2-phenylethyl ester; 2-Propenoic acid, 3-phenyl-, 1-ethenyl-1,5-dimethyl-4-hexen-1-yl ester; Oxacycloheptadec-10-en-2-one; Oxacycloheptadec-8-en-2-one, (8Z)-; 1,7-Dioxacycloheptadecan-8-one; 1,4-Dioxacyclohexadecane-5,16-dione; 1,4-Dioxacycloheptadecane-5,17-dione; Benzoic acid, 2-[(1-hydroxy-3-phenylbutyl)amino]-, methyl ester; and combinations thereof.

In one aspect, said fragrance component comprises one or more volatile fragrance materials, wherein:
a) the volatile fragrance material has a vapor pressure ≥0.001 Torr;
b) the volatile fragrance material is present in an amount of from about 70 wt % to about 99.9 wt %, preferably greater than about 80 wt %, or most preferably greater than about 88%, relative to the total weight of the fragrance component; and
c) combinations thereof.

In one aspect, said volatile fragrance material is selected from the group consisting of:
a) a high volatile fragrance material having a vapor pressure >0.1 Torr;
b) a moderate volatile fragrance material having a vapor pressure in the range of 0.1 Torr to 0.001 Torr; and
c) combinations thereof.

In one aspect, said volatile fragrance material is selected from the group consisting of: Formic acid, methyl ester; Methane, 1,1'-thiobis-; Acetic acid ethyl ester; Propanoic acid, ethyl ester; Acetic acid, 2-methylpropyl ester; Butanoic acid, ethyl ester; 1-Butanol; Butanoic acid, 2-methyl-, ethyl ester; 1-Butanol, 3-methyl-, 1-acetate; Butanoic acid, 2-methyl-, 1-methyl ethyl ester; 2-Heptanone; 2-Hexenal, (2E)-; 1-Butanol, 3-methyl-; 2-Buten-1-ol, 3-methyl-, 1-acetate; 1,3-Dioxolane-2-methanamine, N-methyl-; Bicyclo [3.1.1]hept-2-ene, 2,6,6-trimethyl-, (1R,5R)-; Bicyclo [2.2.1]heptane, 2,2-dimethyl-3-methylene-; 2-Butanethiol, 4-methoxy-2-methyl-; Pentanoic acid, 2-methyl-, ethyl ester; Bicyclo[3.1.1]heptane, 6,6-dimethyl-2-methylene-; 1-Butanol, 3-methyl-, 1-propanoate; 1,6-Octadiene, 7-methyl-3-methylene-; Octanal; 2H-Pyran, 2-ethenyltetrahydro-2,6,6-trimethyl-; 2-Octanone; Hexanoic acid, ethyl ester; 2-Oxabicyclo[2.2.2] octane, 1,3,3-trimethyl-; Benzene, 1-methyl-4-(1-methylethyl)-; Benzene, 1-methoxy-4-methyl-; 1,3,6-Octatriene, 3,7-dimethyl-; Cyclohexene, 1-methyl-4-(1-methylethenyl)-; Cyclohexene, 1-methyl-4-(1-methylethenyl)-, (4R)-; 3-Octanone; Undecanal, 2-methyl-; Acetic acid, hexyl ester; 5-Hepten-2-one, 6-methyl-; 2-Hepten-4-one, 5-methyl-; 3-Hexen-1-ol, 1-acetate, (3Z)-; 3-Hexen-1-ol, 1-acetate; Propanoic acid, 2-hydroxy-, ethyl ester; Butanoic acid, 2-methylbutyl ester; Butanoic acid, 3-methylbutyl ester; 1,4-Cyclohexadiene, 1-methyl-4-(1-methylethyl)-; Thiazole, 2-(2-methylpropyl)-; 3-Hexen-1-ol, (3Z)-; Benzaldehyde; Butanoic acid, 3-oxo-, ethyl ester; 2-Hexen-1-ol, (2E)-; 2-Hexen-1-ol, (2Z)-; Cyclohexane, 3-ethoxy-1,1,5-trimethyl-, cis-(9CI); 2-Pentanone, 4-mercapto-4-methyl-; 2,4,6-Octatriene, 2,6-dimethyl-, (4E,6E)-; Oxirane, 2,2-dimethyl-3-(3-methyl-2,4-pentadien-1-yl)-; 4,7-Octadienoic acid, methyl ester, (4E)-; Carbonic acid, (3Z)-3-hexen-1-yl methyl ester; Hexanoic acid, 2-propen-1-yl ester; 5-Heptenal, 2,6-dimethyl-; Heptanoic acid, ethyl ester; 3-Cyclohexene-1-carboxaldehyde, 2,4-dimethyl-; Benzene, (2,2-dimethoxyethyl)-; 2H-Pyran, tetrahydro-4-methyl-2-(2-methyl-1-propen-1-yl)-; 3-Nonanone; Benzonitrile; 3-Octanol; 1-Hexanol, 3,5,5-trimethyl-, 1-acetate; 4-Heptanol, 2,6-dimethyl-, 4-acetate; Hexanoic acid, 2-methylpropyl ester; Propanoic acid, 2-methyl-, hexyl ester; Cyclohexanecarboxylic acid, 1,4-dimethyl-, methyl ester, trans-; Benzeneacetaldehyde; Butanoic acid, 3-hydroxy-, ethyl ester; Propanedioic acid, 1,3-diethyl ester; Benzoic acid, methyl ester; 1,3,5-Undecatriene; 4-Decenal, (4E)-; 1,3-Dioxane, 2-butyl-4,4,6-trimethyl-; 2-Heptanol, 2,6-dimethyl-; Ethanone, 1-phenyl-; Benzeneacetaldehyde, α-methyl-; Propanoic acid, 2-methyl-, 1,3-dimethyl-3-buten-1-yl ester; 2,6-Nonadienal, (2E,6Z)-; Pyrazine, 2-methoxy-3-(2-methylpropyl)-;

Formic acid, phenylmethyl ester; Benzene, 1-methoxy-4-propyl-; Cyclohexanone, 5-methyl-2-(1-methylethyl)-, (2R,5R)-rel-; Cyclohexanone, 5-methyl-2-(1-methylethyl)-, (2R,5S)-rel-; 2-Nonenal; Cyclohexanone, 2-ethyl-4,4-dimethyl-; Benzene, 1,4-dimethoxy-; Benzene, 1-(ethoxymethyl)-2-methoxy-; Bicyclo[2.2.1]heptan-2-one, 1,7,7-trimethyl-; 2-Hexene, 6,6-dimethoxy-2,5,5-trimethyl-; Decanal; Benzenepropanal, β-methyl-; Benzenemethanol, α-methyl-, 1-acetate; Acetic acid, nonyl ester; Ethanone, 1-(4-methylphenyl)-; 2H-Pyran, 6-butyl-3,6-dihydro-2,4-dimethyl-; Propanoic acid, 2-methyl-, (3Z)-3-hexen-1-yl ester; Benzoic acid, ethyl ester; 3-Octanol, 3,7-dimethyl-, 3-acetate; 1-Hexanol, 5-methyl-2-(1-methylethyl)-, 1-acetate; Cyclohexanol, 3,3,5-trimethyl-, (1R,5R)-rel-; 2-Hexenal, 5-methyl-2-(1-methylethyl)-; 7-Octen-2-ol, 2,6-dimethyl-; Acetic acid, phenylmethyl ester; Cyclohexanone, 2-(1-methylpropyl)-; 3-Octen-1-ol, (3Z)-; Heptanoic acid, 2-propen-1-yl ester; Benzenemethanol; Butanoic acid, 2-methyl-, hexyl ester; 2(3H)-Furanone, 5-ethyldihydro-; Cyclohexaneethanol, 1-acetate; 2-Nonenoic acid, methyl ester; Cyclohexanecarboxylic acid, 2,2-dimethyl-6-methylene-, methyl ester; Butanoic acid, (3Z)-3-hexen-1-yl ester; 2-Octynoic acid, methyl ester; 1,3-Oxathiane, 2-methyl-4-propyl-, (2R,4S)-rel-; Heptanal, 6-methoxy-2,6-dimethyl-; Bicyclo[2.2.1] heptan-2-ol, 1,3,3-trimethyl-, 2-acetate; 1,6-Octadien-3-ol, 3,7-dimethyl-, 3-acetate; 2-Octanol, 2,6-dimethyl-; 1-Octanol; 3-Cyclohexene-1-methanethiol, α,α,4-trimethyl-; Cyclohexanemethanol, α,α,4-trimethyl-, 1-acetate; Cyclohexanol, 2-(1,1-dimethylethyl)-, 1-acetate; Cyclohexanol, 4-(1,1-dimethylethyl)-, 1-acetate; Pyrazine, 2-methoxy-3-(1-methylpropyl)-; Cyclohexanol, 5-methyl-2-(1-methylethenyl)-, (1R,2S,5R)-; 2-Undecanone; Benzenepropanol, α,α-dimethyl-; Bicyclo[2.2.1]heptan-2-ol, 1,7,7-trimethyl-, 2-acetate, (1R,2R,4R)-rel-; 1,6-Octadien-3-ol, 3,7-dimethyl-; Benzeneacetic acid, ethyl ester; Benzeneethanol, α,α-dimethyl-; Cyclopropanecarboxylic acid, (3Z)-3-hexen-1-yl ester; 3-Cyclohexene-1-methanol, 3,5-dimethyl-, 1-acetate; Undecanal; Ethanone, 1-(3-cyclooocten-1-yl)-; Cyclohexanone, 4-(1,1-dimethylethyl)-; 6-Nonen-1-ol, (6Z)-; Benzene, (2-butoxyethyl)-; Cyclohexanecarboxylic acid, 2,2,6-trimethyl-, ethyl ester, (1R,6S)-rel-; Benzeneethanol; 2,6-Octadienal, 3,7-dimethyl-, (2Z)-; 2,6-Octadienal, 3,7-dimethyl-; Cyclohexanol, 5-methyl-2-(1-methylethyl)-, 1-acetate, (1R,2S,5R)-rel-; Benzoic acid, 2-hydroxy-, methyl ester; Benzene, 1-methoxy-4-(1E)-1-propen-1-yl-; 2,6-Octadiene, 1,1-dimethoxy-3,7-dimethyl-; Cyclohexanemethanol, α,3,3-trimethyl-, 1-formate; 2-Decenal, (2E)-; 3-Cyclopentene-1-acetonitrile, 2,2,3-trimethyl-; 2-Cyclohexen-1-one, 2-methyl-5-(1-methylethenyl)-, (5R)-; Cyclohexanone, 4-(1,1-dimethylpropyl)-; 2-Cyclohexen-1-one, 3-methyl-5-propyl-; Benzonitrile, 4-(1-methylethyl)-; 2,6-Nonadienenitrile; Butanoic acid, 2-methyl-, (3Z)-3-hexen-1-yl ester; Benzene, 1-(cyclopropylmethyl)-4-methoxy-; 2-Nonynoic acid, methyl ester; Acetic acid, 2-phenylethyl ester; Cyclohexanol, 2-(1,1-dimethylethyl)-; 2,6-Nonadien-1-ol; Propanoic acid, 2-methyl-, phenylmethyl ester; Bicyclo[2.2.1]heptan-2-ol, 1,2,3,3-tetramethyl-, (1R,2R,4S)-rel-; Benzaldehyde, 4-(1-methylethyl)-; 2,5-Octadien-4-one, 5,6,7-trimethyl-, (2E)-; 3-Cyclohexen-1-ol, 4-methyl-1-(1-methylethyl)-; 3-Cyclohexene-1-methanol, 2,4,6-trimethyl-; Pentanoic acid, (3Z)-3-hexen-1-yl ester; Bicyclo[2.2.1]heptan-2-ol, 1,7,7-trimethyl-, 2-propanoate, (1R,2R,4R)-rel-; Benzene, 1-methyl-4-(1-methylethyl)-2-(1-propen-1-yl)-; 2,4-Nonanedione, 3-methyl-; 3-Cyclohexene-1-propanal, β,4-dimethyl-; 1-Hexanol, 5-methyl-2-(1-methylethyl)-, (2R)-; 3-Heptanone, 5-methyl-, oxime; 2(3H)-Furanone, 5-butyldihydro-; 1-Nonanol; Acetic acid, 2-(3-methylbutoxy)-, 2-propen-1-yl ester; Bicyclo[2.2.1]heptan-2-ol, 1,7,7-trimethyl-, (1S,2R,4S)-; Bicyclo[2.2.1]heptan-2-ol, 1,7,7-trimethyl-, (1R,2R,4R)-rel-; Cyclohexanol, 2-(1,1-dimethylpropyl)-, 1-acetate; 3-Cyclohexene-1-methanol, α,α,4-trimethyl-, 1-acetate; Cyclohexanemethanol, α,α,4-trimethyl-; 10-Undecenal; 1-Octanol, 3,7-dimethyl-; Furan, tetrahydro-2,4-dimethyl-4-phenyl-; Benzene, [2-(3-methylbutoxy)ethyl]-; Butanoic acid, phenylmethyl ester; Benzoic acid, 2-hydroxy-, ethyl ester; Cyclohexanol, 4-(1,1-dimethylethyl)-; 1,6-Octadien-3-ol, 3,7-dimethyl-, 3-formate; Dodecanal; 3,6-Nonadien-1-ol, (3Z,6Z)-; Decanenitrile; Cyclohexanol, 5-methyl-2-(1-methylethyl)-, (1R,2S,5R)-; Propanoic acid, 2-methyl-, 4-methylphenyl ester; Propanoic acid, 2-methyl-, (1R,2S,4R)-1,7,7-trimethylbicyclo[2.2.1]hept-2-yl ester, rel-; Acetaldehyde, 2-(4-methylphenoxy)-; 2-Butenoic acid, 2-methyl-, (3Z)-3-hexen-1-yl ester, (2E)-; Bicyclo[3.1.1]hept-2-ene-2-propanal, 6,6-dimethyl-; 2-Nonanol, 6,8-dimethyl-; Cyclohexanol, 1-methyl-3-(2-methylpropyl)-; 1H-Indole; 2-Undecenal; 2H-Pyran-2-one, 4,6-dimethyl-; 3-Cyclohexene-1-methanol, α,α,4-trimethyl-; 3-Hepten-2-one, 3,4,5,6,6-pentamethyl-, (3Z)-; 2(3H)-Furanone, 5-butyldihydro-4-methyl-; 7-Octen-2-ol, 2,6-dimethyl-, 2-acetate; 2-Propenal, 3-phenyl-; 1,6-Octadien-3-ol, 3,7-dimethyl-, 3-propanoate; 1,6-Nonadien-3-ol, 3,7-dimethyl-, 3-acetate; Cyclopentanone, 2,2,5-trimethyl-5-pentyl-; 2,6-Octadien-1-ol, 3,7-dimethyl-, 1-acetate, (2Z)-; 2,6-Octadien-1-ol, 3,7-dimethyl-, 1-acetate, (2E)-; Undecane, 1,1-dimethoxy-2-methyl-; Benzenemethanol, α-methylene-, 1-acetate; Benzaldehyde, 4-methoxy-; Cyclohexanol, 5-methyl-2-(1-methylethenyl)-, 1-acetate, (1R,2S,5R)-; 6-Octenenitrile, 3,7-dimethyl-;6-Octen-2-ol, 2,6-dimethyl-; Benzene, 1,1'-oxybis-; Benzoic acid, butyl ester; 5,8-Methano-2H-1-benzopyran, 6-ethylideneoctahydro-; Cyclohexanepropanol, α,α-dimethyl-; Benzenepropanal, β-methyl-3-(1-methylethyl)-; Benzenemethanol, 4-methoxy-, 1-acetate; Phenol, 2-ethoxy-4-methyl-; Benzene, [2-(1-propoxyethyl)ethyl]-; 7-Octen-1-ol, 3,7-dimethyl-; Bicyclo[4.3.1]decane, 3-methoxy-7,7-dimethyl-10-methylene-; Propanoic acid, 2-(1,1-dimethylpropoxy)-, propyl ester, (2S)-; Benzoic acid, 2-(methylamino)-, methyl ester; 6-Octen-1-ol, 3,7-dimethyl-, (3S)-; 7-Octen-2-ol, 2-methyl-6-methylene-; 4,6-Octadien-3-ol, 3,7-dimethyl-; 5-Oxatricyclo[8.2.0.04,6]dodecane, 4,9,12,12-tetramethyl-; 2-Cyclohexene-1-carboxylic acid, 2-ethyl-6,6-dimethyl-, ethyl ester; 3-Buten-2-one, 4-(2,6,6-trimethyl-1-cyclohexen-1-yl)-, (3E)-; 4,7-Methano-1H-inden-5-ol, octahydro-, 5-acetate; Benzoic acid, 2-amino-, methyl ester; Spiro[1,3-dioxolane-2,8' (5'H)-[2H-2,4a]methanonaphthalene], hexahydro-1',1',5',5'-tetramethyl-, (2'S,4'aS, 8'aS)-(9CI); 3-Buten-2-one, 4-(2,6,6-trimethyl-2-cyclohexen-1-yl)-, (3E)-; Benzeneethanol, α,α-dimethyl-, 1-acetate; 4,7-Methano-1H-inden-5-ol, 3a,4,5,6,7,7a-hexahydro-, 5-acetate; 6-Octen-1-ol, 3,7-dimethyl-, 1-acetate; 2H-Pyran, tetrahydro-2-methyl-4-methylene-6-phenyl-, Bicyclo[3.3.1]nonane, 2-ethoxy-2,6,6-trimethyl-9-methylene-; 2,6-Octadien-1-ol, 3,7-dimethyl-, (2E)-; Bicyclo[7.2.0]undec-4-ene, 4,11,11-trimethyl-8-methylene-, (1R,4E,9S)-; 1H-3a,7-Methanoazulene, octahydro-6-methoxy-3,6,8,8-tetramethyl-, (3R,3aS,6S,7R,8aS)-; Bicyclo[7.2.0]undec-4-ene, 4,11,11-trimethyl-8-methylene-, (1R,4E,9 S)-; 1H-Inden-1-one, 2,3-dihydro-2,3,3-trimethyl-;2-Propanol, 1,1'-oxybis-, 2-Octanol, 7-methoxy-3,7-dimethyl-;4,9-Decadienal, 4,8-dimethyl-; 3-Hexenoic acid, (3Z)-3-hexen-1-yl ester, (3Z)-; Bicyclo[2.2.1]hept-5-ene-2-carboxylic acid, 3-(1-methylethyl)-, ethyl ester, (1R,2S,3S,4S)-rel-; 2-Propen-1-ol, 3-phenyl-, Propanoic acid, 2-methyl-, 1-ethenyl-1,5-dimethyl-4-hexen-1-yl ester; Ethanol, 2-phenoxy-, 1-propanoate; 2-Propenoic acid, 3-phenyl-, methyl ester; Benzenepropanal, 2-ethyl-α,α-dimethyl-; Propanoic acid, decyl ester; Benzene, 1,2-dimethoxy-4-(1-propen-1-yl)-; 3-Decen-5-ol, 4-methyl-; Phenol, 2-methoxy-4-(2-propen-1-yl)-; 1-Propanone, 1-[2-methyl-5-(1-methylethyl)-2-cyclohexen-1-yl]-; 1,3-Benzodioxole-5-carboxaldehyde; 2-Dodecenal; 2-Dodecenal, (2E)-; Benzenepropanal, 4-methoxy-α-methyl-; 1,4-Cyclohexanedicarboxylic acid, 1,4-dimethyl ester; 2-Buten-1-one, 1-(2,6,6-trimethyl-3-cyclohexen-1-yl)-; 2-Butanone, 4-(2,6,6-trimethyl-1-cyclohexen-1-yl)-; 2-Propenenitrile, 3-phenyl-, (2E)-; Propanoic acid, 2-methyl-, 2-phenylethyl ester; 2-Cyclopenten-1-one, 3-methyl-2-(2Z)-2-penten-1-yl-; Acetaldehyde, 2-[(3,7-dimethyl-6-octen-1-yl)oxy]-; 1-Cyclohexene-1-ethanol, 4-(1-methylethyl)-, 1-formate; 2,4-Decadienoic acid, ethyl ester, (2E,4Z)-; 2-Propen-1-ol, 3-phenyl-, 1-acetate; Naphtho[2,1-b] furan, dodecahydro-3a,6,6,9a-tetramethyl-, (3aR,5aS, 9aS,9bR)-; Benzenepropanal, 4-(1,1-dimethylethyl)-; 1,4-Methanonaphthalen-5(1H)-one, 4,4a,6,7,8,8a-hexahydro-; Dodecanoic acid, 12-hydroxy-, λ-lactone (6CI,7CI); 1,12-; Cyclohexanepropanoic acid, 2-propen-1-yl ester; 2(3H)-Furanone, 5-hexyldihydro-5-methyl-; 2,6-Nonadienenitrile, 3,7-dimethyl-; 10-Undecenoic acid, ethyl ester; Benzenepropanal, α-methyl-4-(1-methylethyl)-; 1-Oxaspiro[4.5] decan-2-one, 8-methyl-; 2(3H)-Furanone, dihydro-5-pentyl-; 2(3H)-Furanone, 5-hexyldihydro-; 2-Buten-1-one, 1-(2, 6,6-trimethyl-2-cyclohexen-1-yl)-, (2E)-; 2-Buten-1-one, 1-(2,4,4-trimethyl-2-cyclohexen-1-yl)-, (2E)-; 2H-Pyran-2-one, tetrahydro-6-pentyl-; Benzenepropanal, 4-ethyl-α,α-dimethyl-; 1,3-Benzodioxole, 5-(diethoxymethyl)-; 4-Penten-1-one, 1-(5,5-dimethyl-1-cyclohexen-1-yl)-; Bicyclo[3.1.1]hept-2-ene-2-ethanol, 6,6-dimethyl-, 2-acetate; 2-Propenoic acid, 3-phenyl-, ethyl ester; 1,3-Dioxane, 2,4, 6-trimethyl-4-phenyl-; Cyclododecane, (methoxymethoxy)-; Bicyclo[3.1.1]hept-2-ene-2-propanal, α,α,6,6-tetramethyl-; 2(3H)-Benzofuranone, hexahydro-3, 6-dimethyl-; Benzeneacetonitrile, 4-(1,1-dimethylethyl)-; 2-Buten-1-one, 1-(2,6,6-trimethyl-1-cyclohexen-1-yl)-; 1,4-Methanonaphthalen-6(2H)-one, octahydro-7-methyl-; Bicyclo[3.2.1]octan-8-one, 1,5-dimethyl-, oxime; Benzenepentanol, γ-methyl-; Cyclohexene, 4-(1,5-dimethyl-4-hexen-1-ylidene)-1-methyl-; Phenol, 2-methoxy-4-propyl-; Benzoic acid, 2-hydroxy-, 2-methylpropyl ester; 2H-1-Benzopyran-2-one, octahydro-;Cyclohexanone, 2-(1-mercapto-1-methylethyl)-5-methyl-; 2-Oxiranecarboxylic acid, 3-methyl-3-phenyl-, ethyl ester; 3-Cyclohexene-1-carboxaldehyde, 4-(4-methyl-3-penten-1-yl)-; Propanoic acid, 2-methyl-, 2-phenoxyethyl ester; Indeno[1,2-d]-1,3-dioxin, 4,4a,5,9b-tetrahydro-; 2H-Pyran-4-ol, tetrahydro-4-methyl-2-(2-methylpropyl)-; Cyclohexanebutanal, α,2,6,6-tetramethyl-; 1,6-Nonadien-3-ol, 3,7-dimethyl-; 3-Buten-2-one, 4-(2,2,6-trimethyl-7-oxabicyclo[4.1.0]hept-1-yl)-; Phenol, 2-methoxy-4-(1-propen-1-yl)-; 2(3H)-Furanone, 5-hexyldihydro-4-methyl-; 1-Penten-3-one, 1-(2,6,6-trimethyl-2-cyclohexen-1-yl)-; 2-Buten-1-one, 1-(2,6,6-trimethyl-1,3-cyclohexadien-1-yl)-; 2-Cyclopenten-1-one, 2-hydroxy-3-methyl-; Propanoic acid, 2,2-dimethyl-, 2-phenylethyl ester; Dodecanenitrile; 6-Octen-1-ol, 3,7-dimethyl-, 1-propanoate; Benzenepentanal, 3-methyl-; Acetic acid, 2-phenoxy-, 2-propen-1-yl ester; Benzenepropanal, 4-(1,1-dimethylethyl)-α-methyl-, 4,7-Methano-1H-indene-2-carboxaldehyde, octahydro-5-methoxy-; Pentitol, 1,5-anhydro-2,4-dideoxy-2-pentyl-, 3-acetate; Cyclododecane, (ethoxymethoxy)-; 3-Buten-2-one, 4-(2,5,6,6-tetramethyl-2-cyclohexen-1-yl)-; Indeno[4,3a-b]furan, decahydro-2,2,7,7, 8,9,9-heptamethyl-; Quinoline, 6-(1-methylpropyl)-; Carbonic acid, 4-cycloocten-1-yl methyl ester; 1H-Indene-5-propanal, 2,3-dihydro-3,3-dimethyl-; 3-Cyclohexene-1-carboxaldehyde, 1-methyl-3-(4-methyl-3-penten-1-yl)-; 6-Oxabicyclo[3.2.1]octane, 5-methyl-1-(2,2,3-trimethyl-3-cyclopenten-1-yl)-; 2H-Pyran-2-one, tetrahydro-6-(3-penten-1-yl)-; 2,4,7-Decatrienoic acid, ethyl ester; Butanoic acid, 3-methyl-, 2-phenylethyl ester; Spiro[1,4-methanonaphthalene-2(1H),2'-oxirane], 3,4,4a,5,8,8a-hexahydro-3',7-dimethyl-; Ethanol, 2-[[(1R,2R,4R)-1,7,7-trimethylbicyclo[2.2.1]hept-2-yl]oxy]-, rel-; Phenol, 2-methoxy-4-(1-propen-1-yl)-, 1-acetate; 2H-Indeno[4,5-b]furan, decahydro-2,2,6,6,7,8,8-heptamethyl-; Acetic acid, 2-(cyclohexyloxy)-, 2-propen-1-yl ester; Octanal, 7-hydroxy-3,7-dimethyl-; 1,6-Heptadien-3-one, 2-cyclohexyl-; 5-Thiazoleethanol, 4-methyl-; 1,4-Cyclohexanedicarboxylic acid, 1,4-diethyl ester; 2(3H)-Furanone, 5-heptyldihydro-; 1,3-Benzodioxole-5-propanal, αmethyl-; 4H-Inden-4-one, 1,2, 3,5,6,7-hexahydro-1,1,2,3,3-pentamethyl-; Cyclohexanone, 4-(1-ethoxyethenyl)-3,3,5,5-tetramethyl-,Benzenepropanenitrile, α-ethenyl-α-methyl-; 9-Undecenal, 2,6,10-trimethyl-; Pyridine, 2-(3-phenylpropyl)-; Indeno[1,2-d]-1,3-dioxin, 4,4a,5,9b-tetrahydro-2,4-dimethyl-;Propanoic acid, 2-methyl-, 3a,4,5,6,7,7a-hexahydro-4,7-methano-1H-inden-5-yl ester; 1-Naphthalenol, 1,2,3,4,4a,7,8,8a-octahydro-2, 4a,5,8a-tetramethyl-, 1-formate; Benzenepropanol, β,β,3-trimethyl-; 2-Cyclohexen-1-one, 4-(2-buten-1-ylidene)-3,5, 5-trimethyl-; 3-Hexen-1-ol, 1-benzoate, (3Z)-; Benzaldehyde, 4-hydroxy-3-methoxy-; 1H-3a, 7-Methanoazulen-6-ol, octahydro-3,6,8,8-tetramethyl-, 6-acetate, (3R, 3aS,6R,7R,8aS)-; 4,7-Methano-1H-inden-6-ol, 3a,4,5,6,7, 7a-hexahydro-8,8-dimethyl-, 6-propanoate; 2-Oxiranecarboxylic acid, 3-phenyl-, ethyl ester; 4H-4a,9-Methanoazuleno[5,6-d]-1,3-dioxole, octahydro-2,2,5,8,8, 9a-hexamethyl-, (4aR,5R,7aS,9R)-; 1H-Indene-2-methanol, 2,3-dihydro-2,5-dimethyl-; Butanoic acid, 1,1-dimethyl-2-phenylethyl ester; Cyclododeca[c]furan, 1,3,3a,4,5,6,7,8,9, 10,11,13a-dodecahydro-; Benzenebutanenitrile, α,α,γ-trimethyl-; 2-Butanone, 4-(1,3-benzodioxol-5-yl)-; Benzoic acid, 4-hydroxy-3-methoxy-, methyl ester; 3-Cyclopentene-1-butanol, (3,2,2,3-tetramethyl-2-Methyl-4-(2,2,3-trimethyl-3-cyclopenten-1-yl)butanol; 2-Butenal, 2-methyl-4-(2, 6,6-trimethyl-1-cyclohexen-1-yl)-; 2-Naphthalenol, decahydro-2,5,5-trimethyl-;1,7-Octanediol, 3,7-dimethyl-; 2H-1-Benzopyran-2-one; 1,3-Dioxolane, 2-[6-methyl-8-(1-methylethyl)bicyclo[2.2.2]oct-5-en-2-yl]-; Propanoic acid, 2,2-dimethyl-, 3a,4,5,6,7,7a-hexahydro-4,7-methano-1H-inden-6-yl ester; Butanoic acid, (2E)-3,7-dimethyl-2,6-octadien-1-yl ester; 2-Butanone, 4-(4-hydroxyphenyl)-; 10-Undecenoic acid, butyl ester; and combinations thereof.

In one aspect, said perfume composition comprises ethanol in the amount of from ab out 50 wt % to about 80 wt %, or from about 55 wt % to about 75 wt %, relative to the total weight of the composition.

In one aspect, said perfume composition comprises one or more non-odorous fragrance co-modulators selected from the group consisting of:
a) Isocetyl alcohol, for example CERAPHYL ICA;
b) PPG-3 myristyl ether for example, Tegosoft APM and/or Varonic APM;
c) Neopentyl glycol diethylhexanoate for example Schercemol NGDO; and
d) mixtures thereof.

wherein the one or more non-odorous fragrance co-modulators are present in the amount of from about 0.05 wt % to about 10 wt %, preferably from about 0.5 wt % to about 6 wt %, relative to the total weight of the composition.

In one aspect, said perfume composition comprises isocetyl alcohol.

In one aspect, said perfume composition the non-odorous fragrance modulators are formed of at least 50 wt % of PPG-20 Methyl Glucose Ether, relative to the combined weight of the non-odorous fragrance modulators and the non-odorous fragrance co-modulators.

In one aspect, said perfume composition, said composition comprises:
at least one low volatile fragrance material having a vapor pressure <0.001 Torr, in the amount of from about 0.1 wt % to about 30 wt %, relative to the total weight of the fragrance component;
(i) at least one volatile fragrance material having a vapor pressure ≥0.001 Torr in the amount of from about 70 wt % to about 99.9 wt %, relative to the total weight of the fragrance component; and
(ii) a non-odorous fragrance modulator formed of an alkoxylated methyl glucoside, preferably PPG-20 Methyl Glucose Ether, in the amount of from about 0.1 wt % to about 20 wt %, relative to the total weight of the composition.

In one aspect, of said perfume composition said composition comprises one or more non-odorous fragrance co-modulators selected from the group consisting of Isocetyl alcohol, for example, CERAPHYL ICA; PPG-3 myristyl ether for example, Tegosoft APM and/or Varonic APM; Neopentyl glycol diethylhexanoate, for example, Schercemol NGDO; or mixtures thereof, in one aspect in the amount of from about 0.5 wt % to about 6 wt %, relative to the total weight of the composition.

In one aspect, said perfume composition is in the form of a perfume, an eau de toilette, an eau de parfum, a cologne, a body splash, or a body spray.

In one aspect, a perfume raw material having a two week anti-habituation index of at least 0, 1, 2, 3, or 4; a four week anti-habituation index of at least 0, 1, 2, 3 or 4; a two week anti-habituation index of 0, 1, 2, 3, or 4; and/or a four week anti-habituation index of 0, 1, 2, 3, or 4, with the proviso that said perfume raw material is not:

a) said perfume raw material comprising a thiol moiety is selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; Ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl)prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enylsulfanylprop-1-ene; 1-methoxyhexane-3-thiol; ethyl 2-sulfanylpropanoate; 1-(prop-2-enyldisulfanyl)propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo[3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; 2-methyl-2-sulfanylpentan-1-ol; and mixtures thereof;

b) said perfume raw material comprising a sulfide moiety is selected from the group consisting of 1-butylsulfanylbutane; ethyl 3-methylsulfanylpropanoate; 2-(methylsulfanylmethyl)furan; methyl sulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methyl sulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enylpropanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methylfuran-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl)methanethioate; 1,2,4-trithiolane; 2-methylthiolan-3-one; 4-methylsulfanylbutan-1-ol; S-butan-2-yl 3-methylbutanethioate; S-butan-2-yl3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl) ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl) butan-2-one; 3-methylsulfanylbutanoic acid; 2-methylsulfanylpyrazine; 2-methyl-3-methyl sulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methyl sulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate and mixtures thereof;

c) said perfume raw material comprising a thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; 4-methyl-2-propan-2-yl-1, 3-thiazole; and mixtures thereof;

d) said perfume raw material comprising a pyrazine moiety is selected from the group consisting of 2-methoxy-3-(2-methylpropyl)pyrazine; 2,3-dimethylpyrazine; 1-pyrazin-2-ylethanone; 2-methyl-3-methylsulfanylpyrazine; Pyrazine; 2-methylpyrazine; 2-ethenylpyrazine; 2-ethylpyrazine; 2,6-dimethylpyrazine; 2,5-dimethylpyrazine; 2-prop-1-en-2-ylpyrazine; 2-propan-2-ylpyrazine; 2-methoxypyrazine; 2-ethenyl-5-methylpyrazine; 2-ethyl-5-methylpyrazine; 2-Ethyl-6-methylpyrazine; 2-Ethyl-3-Methyl-Pyrazine; 2-propylpyrazine; 2,3,5-trimethylpyrazine; 2-tert-butylpyrazine; pyrazin-2-amine; 2-(2-methylpropyl)pyrazine; 2-methyl-5-propan-2-ylpyrazine; 2-(methoxymethyl)pyrazine; 2,3-diethylpyrazine; 2-ethyl-3,(5 OR 6)-dimethylpyrazine; 2-ethyl-3,5-dimethylpyrazine; 3-ethyl-2,5-dimethylpyrazine; 3-ethyl-2,5-dimethylpyrazine; 2-ethyl-3,5-dimethylpyrazine; 2-methyl-3-propylpyrazine; 2,3,5,6-tetramethylpyrazine; 7-methyl-6,7-dihydro-5H-cyclopenta[b]pyrazine; 2-methylsulfanylpyrazine; 2-methyl-3-methylsulfanylpyrazine; 2-ethoxy-3-ethylpyrazine; 2-Isobutyl-3-methylpyrazine; pyrazin-2-ylmethanethiol; 3,5-dimethyl-2-propylpyrazine; 2-ethyl-3-methoxypyrazine; 2-ethoxy-3-methylpyrazine; 2-ethyl-5-methoxypyrazine; 5,6,7,8-tetrahydroquinoxaline; 2-ethoxy-3-propan-2-ylpyrazine; 2-(methylsulfanylmethyl)pyrazine; 3,5-dimethyl-2-(2-methylpropyl)pyrazine; 2,3-diethyl-5-methylpyrazine; 3,5-Diethyl-2-methylpyrazine; 2,5-dimethyl-3-(2-methylpropyl)pyrazine; 2-methyl-6-propoxypyrazine; 2-(2-methylpropoxy)pyrazine; 1-(3-methylpyrazin-2-yl)ethanone; 2-methyl-3-methylsulfanylpyrazine; 2-methoxy-3-propan-2-ylpyrazine; quinoxaline; 3-butyl-2,5-dimethylpyrazine; 2-butyl-3,5-dimethylpyrazine; 2-pyrazin-2-ylethanethiol; 1-(3-ethylpyrazin-2-yl)ethanone; 1-(3,5-dimethylpyrazin-2-yl)ethanone; 2-butan-2-yl-3-methoxypyrazine; 2-methylquinoxaline; 5-Methylquinoxaline; 2-methoxy-3-(4-methylpentyl)pyrazine; 2,3-dimethylquinoxaline; 2-(cyclohexylmethyl)pyrazine; 2-[(furan-2-ylmethyl)sulfanyl]-5-methylpyrazine and mixtures thereof;

e) said perfume raw material comprising a nitrile moiety is selected from the group consisting of 3,7-dimethyloct-6-enenitrile, 3-(4-ethylphenyl)-2,2-dimethylpropanenitrile; and mixtures thereof;

f) said perfume raw material comprising a indole moiety is selected from the group consisting of 1H-indole, 3-methyl-1H-indole; and mixtures thereof;

g) said perfume raw material comprising a oxathiane moiety is selected from the group consisting of (2R, 4S)-2-methyl-4-propyl-1,3-oxathiane, 2-methyl-4-propyl-1,3-oxathiane, 2-pentyl-4-propyl-1,3-oxathiane; and mixtures thereof;

h) said perfume raw material comprising a oxime moiety is selected from the group consisting of (NE)-N-[(6E)-2,4,4,7-tetramethylnona-6,8-dien-3-ylidene]hydroxylamine; N-(5-methylheptan-3-ylidene)hydroxylamine, and mixtures thereof;

i) said perfume raw material comprising a amine moiety is selected from the group consisting of methyl 2-aminobenzoate, pentane-1,5-diamine; 6-methyl-7-Oxa-1-thia-4-azaspiro[4.4]nonane; and mixtures thereof is disclosed.

In one aspect, any of said perfume raw materials disclosed herein may be present in a perfume or a composition comprising said perfume at a level below their respective odor detection thresholds. In short, perfumes and compositions comprising same may comprise one or more, for example 1, 2, 3, 4, 5, 6, 7, 8, 9, or 10 etc., of the anti-habituating perfume raw materials at levels below the respective odor detection thresholds of such anti-habituating perfume raw materials.

Suitable perfumes include perfumes A through G in Table 11 below:

| Perfume Raw Material | Perfume A | Perfume B | Perfume C | Perfume D | Perfume E | Perfume F | Perfume G |
| --- | --- | --- | --- | --- | --- | --- | --- |
| 4-Tertiary Butyl Cyclohexyl Acetate | 2.50% | 2.50% | 3.00% | 3.00% | 3.50% | 3.50% | 3.50% |
| Allyl Caproate | 0.20% | 0.10% | 0.10% | 0.20% | 0.10% | 0.20% | 0.20% |
| Allyl Cyclohexane Propionate | 1.25% | 2.00% | 1.25% | 2.00% | 2.00% | 2.00% | 2.00% |

-continued

| Perfume Raw Material | Perfume A | Perfume B | Perfume C | Perfume D | Perfume E | Perfume F | Perfume G |
|---|---|---|---|---|---|---|---|
| Allyl Heptoate | 3.50% | 2.90% | 3.50% | 3.50% | 4.00% | 3.00% | 3.00% |
| Benzyl Acetate | 3.00% | 3.00% | 3.00% | 2.00% | 2.00% | 2.00% | 3.00% |
| Benzyl Salicylate | 5.00% | 5.00% | 5.00% | 5.00% | 5.00% | 5.00% | 5.00% |
| Beta Gamma Hexenol | 0.20% | 0.15% | 0.10% | 0.20% | 0.15% | 0.10% | 0.20% |
| Castech | 1.00% | 0.90% | 1.00% | 0.95% | 1.25% | 0.90% | 0.85% |
| Cis 3 Hexenyl Acetate | 0.10% | 0.20% | 0.10% | 0.10% | 0.20% | 0.10% | 0.10% |
| Cis Jasmone | 0.10% | 0.10% | 0.10% | 0.20% | 0.10% | 0.10% | 0.10% |
| Cyclopentol Hc 937165 | 0.20% | 0.20% | 0.40% | 0.40% | 0.20% | 0.40% | 0.40% |
| Delta Damascone | 0.10% | 0.20% | 0.10% | 0.20% | 0.10% | 0.10% | 0.10% |
| Dihydro Iso Jasmonate | 1.00% | 1.00% | 1.25% | 0.75% | 1.50% | 1.50% | 0.79% |
| Dihydro Myrcenol | 2.50% | 3.00% | 2.50% | 2.50% | 3.00% | 3.00% | 2.00% |
| Dimethyl Benzyl Carbinyl Acetate | 4.00% | 2.00% | 5.00% | 1.00% | 3.50% | 3.00% | 2.00% |
| Dimethyl Benzyl Carbinyl Butyrate | 1.00% | 2.00% | 1.00% | 1.00% | 0.70% | 1.00% | 2.00% |
| Ethyl 2 Methyl Pentanoate | 0.20% | 0.10% | 0.15% | 0.10% | 0.15% | 0.20% | 0.40% |
| Ethyl Acetoacetate | 1.50% | 2.50% | 2.50% | 1.40% | 1.75% | 1.50% | 2.00% |
| Ethyl Butyrate | 0.10% | 0.10% | 0.25% | 0.25% | 0.20% | 0.20% | 0.10% |
| Ethyl Caproate FCC | 0.50% | 0.40% | 0.40% | 0.50% | 0.50% | 0.50% | 0.50% |
| Ethyl Maltol | 0.75% | 0.50% | 0.75% | 0.50% | 0.50% | 1.00% | 1.00% |
| Ethyl Oenanthate | 0.50% | 0.20% | 0.15% | 0.15% | 0.20% | 0.50% | 0.40% |
| Ethyl-2-Methyl Butyrate | 0.50% | 0.75% | 0.50% | 0.50% | 0.75% | 0.75% | 0.75% |
| Ethylene Brassylate | 3.00% | 4.00% | 4.00% | 5.00% | 3.00% | 3.00% | 3.00% |
| Florhydral | 0.25% | 0.25% | 0.25% | 0.50% | 0.50% | 0.50% | 0.25% |
| Gamma Decalactone | 0.50% | 1.00% | 1.25% | 0.78% | 0.50% | 0.40% | 0.65% |
| Grapefruit Zest #925 (C-Citrus&Allied) | 0.15% | 0.30% | 0.20% | 0.25% | 0.35% | 0.35% | 0.50% |
| Hexamethylindanopyran | 10.00% | 8.00% | 8.00% | 8.00% | 8.00% | 10.00% | 10.00% |
| Hexyl Acetate | 1.25% | 1.75% | 1.75% | 1.50% | 1.00% | 0.50% | 0.50% |
| Hexyl Cinnamic Aldehyde | 7.00% | 8.50% | 10.00% | 10.00% | 5.00% | 5.00% | 7.00% |
| Indolene | 0.10% | 0.10% | 0.10% | 0.20% | 0.10% | 0.10% | 0.20% |
| Ionone Beta | 2.00% | 1.50% | 1.25% | 1.25% | 1.50% | 1.50% | 1.00% |
| Iso E Super Or Wood | 2.50% | 2.00% | 1.50% | 2.00% | 2.00% | 3.00% | 2.50% |
| Italian Mandarin Oil Yellow #10567 | 0.50% | 1.00% | 0.50% | 1.00% | 0.50% | 1.08% | 0.50% |
| Jasmal | 0.50% | 0.40% | 0.40% | 0.50% | 0.40% | 0.50% | 0.40% |
| Labienoxime 10 Opt | 0.85% | 0.75% | 0.70% | 1.00% | 0.80% | 1.00% | 0.75% |
| Ligustral Or Triplal | 0.20% | 0.20% | 0.40% | 0.25% | 0.35% | 0.35% | 0.20% |
| Linalool | 6.00% | 6.00% | 6.00% | 6.00% | 6.00% | 6.50% | 7.00% |
| Linalyl Acetate | 2.00% | 2.00% | 1.00% | 2.00% | 2.00% | 3.00% | 1.00% |
| Linalyl Benzoate | 0.50% | 1.00% | 0.40% | 0.40% | 1.00% | 0.50% | 0.50% |
| Methyl Dihydro Jasmonate | 5.00% | 5.00% | 5.00% | 5.00% | 5.00% | 5.00% | 5.00% |
| Methyl Iso Butenyl Tetrahydro Pyran | 0.05% | 0.02% | 0.02% | 0.02% | 0.05% | 0.02% | 0.01% |
| Methyl Phenyl Carbinyl Acetate | 0.68% | 0.75% | 1.50% | 1.50% | 1.00% | 1.00% | 0.60% |
| Nectaryl | 2.00% | 1.00% | 1.00% | 1.00% | 2.00% | 2.00% | 1.00% |
| Nonalactone | 0.50% | 0.50% | 0.75% | 0.25% | 0.75% | 0.20% | 0.20% |
| Oil Lemon Brazilcp Select Fcc Enh 15130 | 2.00% | 3.00% | 2.50% | 2.00% | 3.00% | 2.50% | 2.50% |
| Oil Pink Grapefruit California Fcc 15029 | 6.50% | 7.00% | 5.50% | 7.00% | 5.50% | 6.50% | 6.00% |
| Phenoxy Ethyl Iso Butyrate | 3.00% | 3.00% | 2.00% | 3.00% | 5.00% | 2.00% | 5.00% |
| Prenyl Acetate | 0.20% | 0.25% | 0.40% | 0.25% | 0.35% | 0.45% | 0.40% |
| Sandalore | 0.50% | 0.50% | 0.50% | 0.75% | 1.00% | 1.00% | 1.00% |
| Synambran R 50% In IPM | 0.22% | 0.18% | 0.18% | 0.20% | 0.40% | 0.50% | 0.20% |
| Undecalactone | 7.00% | 4.50% | 4.50% | 5.00% | 5.00% | 4.50% | 5.00% |
| Undecavertol | 0.10% | 0.50% | 0.10% | 0.50% | 0.10% | 1.00% | 0.50% |
| Veloutone | 0.25% | 0.25% | 0.25% | 0.50% | 0.50% | 0.50% | 0.25% |
| Verdox | 5.00% | 5.00% | 6.00% | 6.00% | 6.00% | 5.00% | 6.00% |
| TOTALS: | 100% | 100% | 100% | 100% | 100% | 100% | 100% |

Thus, a perfume selected from the group consisting of Table 1 perfumes A through G is disclosed.

Suitable perfume raw materials may be obtained from: Symrise GmbH, with offices located at Muhlenfeldstrasse 1, Holzminden, 37603, Germany; International Flavors & Fragrances Inc., a New York corporation having an address at 521 W 57th Street, New York, NY 10019; Givaudan Suisse SA a Swiss corporation having an address at 1214 Vernier, Switzerland; Firmenich Inc., with offices located at 250 Plainsboro Rd., Plainsboro Township, NJ 08536, United States; and Takasago International Corporation (USA), with offices located at 4 Volvo Drive, Rockleigh, NJ 07647, United States.

Compositions

The perfumes disclosed in the present specification may be used in any combination in any type of consumer product, cleaning and/or treatment composition, fabric and hard surface cleaning and/or treatment composition, detergent, and highly compact detergent. In one aspect, composition comprising a consumer product material and, based on total composition weight, a perfume raw material selected from the group consisting of:

a) from about 0.00000001% to about 1%, from about 0.0000001% to about 0.5%, from about 0.0000005% to about 0.25%, from about 0.000001% to about 0.1%, from about 0.0000025% to about 0.08%, of a perfume raw material comprising a thiol moiety;

b) from about 0.00000001% to about 1%, from about 0.00000001% to about 0.5%, from about 0.0000005% to about 0.25%, from about 0.000001% to about 0.1%, from about 0.0000025% to about 0.05%, of a perfume raw material comprising a sulfide moiety;

c) from about 0.0000001% to about 1%, from about 0.0000005% to about 0.5%, from about 0.000001% to about 0.25%, from about 0.00050% to about 0.1%, from about 0.0001% to about 0.01%, of a perfume raw material comprising a thiazole moiety;

d) from about 0.000000005% to about 0.5%, from about 0.00000001% to about 0.25%, from about 0.00000005% to about 0.2%, from about 0.0000001% to about 0.1%, from about 0.0000005% to about 0.05%, of a perfume raw material comprising a pyrazine moiety;

e) from about 0.000001% to about 2%, from about 0.00001% to about 1.5%, from about 0.0001% to about 1%, from about 0.001% to about 0.5%, from about 0.01% to about 0.25%, of a perfume raw material comprising a nitrile moiety;

f) from about 0.0000001% to about 1%, from about 0.000001% to about 0.7%, from about 0.00001% to about 0.4%, from about 0.0001% to about 0.2%, from about 0.001% to about 0.1%, of a perfume raw material comprising an indole moiety;

g) from about 0.00000001% to about 1%, from about 0.0000001% to about 0.5%, from about 0.0000005% to about 0.25%, from about 0.000001% to about 0.1%, from about 0.0000025% to about 0.08%, of a perfume raw material comprising an oxathiane moiety;

h) from about 0.000001% to about 1%, from about 0.00001% to about 0.75%, from about 0.0001% to about 0.5%, from about 0.0005% to about 0.25%, from about 0.001% to about 0.1%, of a perfume raw material comprising an oxime moiety;

i) from about 0.000001% to about 2%, from about 0.00001% to about 1.5%, from about 0.0001% to about 1%, from about 0.001% to about 0.5%, from about 0.01% to about 0.25%, of a perfume raw material comprising an amine moiety;

j) from about 0.000000005% to about 0.5%, from about 0.00000001% to about 0.25%, from about 0.00000005% to about 0.2%, from about 0.0000001% to about 0.1%, from about 0.0000005% to about 0.05%, of a perfume raw material comprising an isothiocyanate;

k) from about 0.000000005% to about 0.5%, from about 0.00000001% to about 0.25%, from about 0.00000005% to about 0.2%, from about 0.0000001% to about 0.1%, from about 0.0000005% to about 0.05%, of a perfume raw material comprising a diamine moiety;

l) from about 0.0000001% to about 1%, from about 0.0000005% to about 0.5%, from about 0.000001% to about 0.25%, from about 0.00005% to about 0.1%, from about 0.0001% to about 0.01%, of a perfume raw material comprising oxygen, sulfur, and nitrogen; and m) mixtures thereof, with the proviso that the sum of the percentage of said perfume raw materials cannot exceed 100%, is disclosed.

In one aspect, of said composition, said consumer product material is selected from the group consisting of an antiperspirant active, antimicrobial deodorant active, monohydric alcohol, polyhydric alcohol, petrolatum, an emulsifier, a foaming surfactant, a hair conditioner, gylcerine and mixtures thereof.

In one aspect, a composition comprising a consumer product material and a perfume having:

a) a two week anti-habituation index of at least 0, 1, 2, 3 or 4;
b) a four week anti-habituation index of at least 0, 1, 2, 3 or 4;
c) a two week anti-habituation index of 0, 1, 2, 3, or 4; and/or
d) a four week anti-habituation index of 0, 1, 2, 3 or 4 is disclosed.

In one aspect, a composition comprising a consumer product material and one or more perfume raw materials, said composition having:

a) a two week anti-habituation index of at least 0, 1, 2, 3, or 4;
b) a four week anti-habituation index of at least 0, 1, 2, 3 or 4;
c) a two week anti-habituation index of 0, 1, 2, 3 or 4; and/or
d) a four week anti-habituation index of 0, 1, 2, 3 or 4 is disclosed.

In one aspect, a consumer product comprising, based on total consumer product weight, from about 0.0001% to about 100% of a neat perfume and/or perfume raw disclosed herein, the balance of said consumer product comprising an adjunct ingredient and/or a perfume delivery system comprising a perfume, an encapsulate disclosed herein, a cyclic oligosaccharide complex disclosed herein and/or a perfume raw material disclosed herein, is disclosed.

In one aspect, a cleaning and/or treatment composition comprising based on total cleaning and treatment products weight from about 0.0001% to about 25% of a perfume, an encapsulate disclosed herein, a cyclic oligosaccharide complex disclosed herein and/or perfume raw disclosed herein and an adjunct ingredient is disclosed.

In one aspect, a fabric and/or hard surface cleaning and/or treatment composition comprising, based on total fabric and/or hard surface cleaning and/or treatment composition weight of from about 0.00001% to about 25% of a perfume an encapsulate disclosed herein, a cyclic oligosaccharide complex disclosed herein and/or perfume raw disclosed herein and an adjunct ingredient, is disclosed.

In one aspect, a detergent comprising, based on total fabric and/or hard surface cleaning and/or treatment composition weight of from about 0.00001% to about 25% of a perfume, an encapsulate disclosed herein, a cyclic oligosaccharide complex disclosed herein and/or perfume raw disclosed herein and an adjunct ingredient, is disclosed.

In one aspect, a highly compacted consumer product comprising, based on total highly compacted consumer product composition weight, from about 0.00001% to about 25% of a perfume, an encapsulate disclosed herein, a cyclic oligosaccharide complex disclosed herein and/or perfume raw disclosed herein and an adjunct ingredient, is disclosed.

In one aspect, a consumer product comprising, based on total consumer product weight, from about 0.0001% to about 100% of a neat perfume, and/or perfume raw disclosed herein, the balance of said consumer product comprising an adjunct ingredient and/or a perfume delivery system comprising a perfume and/or perfume raw disclosed herein, is disclosed.

In one aspect, a cleaning and/or treatment composition comprising based on total cleaning and treatment composition weight from about 0.0001% to about 25% of a perfume, and/or perfume raw disclosed herein and an adjunct ingredient, is disclosed.

In one aspect, a fabric and/or hard surface cleaning and/or treatment composition comprising, based on total fabric and/or hard surface cleaning and/or treatment composition weight, from about 0.00001% to about 25% of a perfume, and/or perfume raw disclosed herein and an adjunct ingredient, is disclosed.

In one aspect, a detergent comprising based on total detergent weight of from about 0.00001% to about 25% of a perfume, and/or perfume raw disclosed herein and an adjunct ingredient, is disclosed.

In one aspect, a highly compacted consumer product comprising, based on total highly compacted consumer product weight, from about 0.00001% to about 25% of a perfume, and/or perfume raw disclosed herein and an adjunct ingredient, is disclosed.

In one aspect, a deodorant comprising a perfume, an encapsulate disclosed herein, a cyclic oligosaccharide complex disclosed herein and/or perfume raw disclosed herein and, based on total deodorant weight, from about 0.01% to about 75% of an antimicrobial, is disclosed.

In one aspect, said deodorant comprises, based on total deodorant weight, from about 10% to about 75% glycol.

In one aspect, an antiperspirant comprising a perfume, an encapsulate disclosed herein, a cyclic oligosaccharide complex disclosed herein and/or perfume raw disclosed herein and, based on total composition weight, from about 1% to about 25% of an aluminum salt antiperspirant active, is disclosed.

In one aspect, a body wash/shampoo comprising a perfume, an encapsulate disclosed herein, a cyclic oligosaccharide complex disclosed herein and/or perfume raw disclosed herein and a miscellar phase and/or lamellar phase, is disclosed.

In one aspect, a lotion comprising a perfume, an encapsulate disclosed herein, a cyclic oligosaccharide complex disclosed herein and/or perfume raw disclosed herein and a humectants, is disclosed.

In one aspect, said lotion comprises glycerin.

In one aspect, a fabric care composition comprising a perfume, an encapsulate disclosed herein, a cyclic oligosaccharide complex disclosed herein and/or perfume raw disclosed herein, said fabric care composition being selected from the group consisting of detergents, fabric softeners, and laundry additives,
  a) said detergent being:
    (i) a liquid detergent comprising a material selected from an anti-redep polymer, an enzyme, a structurant and mixtures thereof;
    (ii) a powder or granule detergent comprising a material selected from the group consisting of an anti-redep polymer, an enzymes, a bleach and mixtures thereof;
    (iii) a unit dose comprising a material selected from the group consisting of an anti-redep polymer, an enzymes, a bleach, a soluble substrate/film and mixtures thereof
  b) said fabric softener being a liquid, powder or sheet comprising a fabric softener active and an optional structurant;
  c) said laundry additive being:
    (i) a bleach additive comprising a material selected from the group consisting of hypochlorite, hydrogen peroxide and mixtures thereof;
    (ii) a pretreater comprising a material selected from the group consisting of an effervescent, a propellant and mixtures thereof; and
    (iii) an in-wash boosters comprising a material selected from the group consisting of an enzyme, a non-chlorine bleach and mixtures thereof
  is disclosed.

In one aspect, a home care composition comprising a perfume, an encapsulate disclosed herein, a cyclic oligosaccharide complex disclosed herein and/or perfume raw disclosed herein, said home care composition being selected from the group consisting of an automatic dish washing composition, a hand dish washing composition, a hard surface cleaning composition and an air care composition,
  a) said automatic dish washing composition being:
    (i) a liquid or gel comprising a material selected from an anti-redep polymer, an enzyme, a structurant, a shine/sheeting polymer and mixtures thereof;
    (ii) a powder or granule comprising a material selected from the group consisting of an anti-redep polymer, an enzyme, a bleach, a shine/sheeting polymer and mixtures thereof;
    (iii) a unit dose comprising a material selected from the group consisting of an anti-redep polymer, an enzymes, a bleach, a shine/sheeting polymer, a soluble substrate/film and mixtures thereof
  b) said hand dish washing composition comprising a material selected from the group consisting of a anti-bacterial, a hand/skin softener, shine/sheeting polymers and mixtures thereof;
  c) said hard surface cleaning composition comprising a material selected from the group consisting of an anti-bacterial, a strong acid, preferably selected from the group consisting of glycolic acid, citric acid and mixtures thereof, etc., a strong base, preferably selected from the group consisting of a Na hydroxides, a Li hydroxide and mixtures thereof, an effervescent, a propellants, a shine/sheeting polymers and mixtures thereof;
  d) an air care composition comprising a malodor control composition that comprises zinc, cyclodextrin, a propellant and/or mixtures thereof
  is disclosed.

A consumer product comprising, based on total consumer product weight, from about 0.0001% to about 100% of a neat perfume selected from the group consisting of Table 1 perfumes A through G, the balance of consumer product comprising an adjunct ingredient, and/or a perfume delivery system comprising a Table 1 perfume is also disclosed.

A cleaning and/or treatment composition comprising based on total cleaning and treatment products weight from about 0.0001% to about 25% of a perfume selected from the group consisting of Table 1 perfumes A through G and an adjunct ingredient is also disclosed.

A fabric and/or hard surface cleaning and/or treatment composition comprising, based on total fabric and/or hard surface cleaning and/or treatment composition weight of from about 0.00001% to about 25% of a perfume selected from the group consisting of Table 1 perfumes A through G and an adjunct ingredient is also disclosed.

A detergent comprising, based on total fabric and/or hard surface cleaning and/or treatment composition weight of from about 0.00001% to about 25% of a perfume selected from the group consisting of Table 1 perfumes A through G and an adjunct ingredient is also disclosed.

A highly compacted consumer product comprising, based on total highly compacted consumer product composition weight, from about 0.00001% to about 25% of a perfume selected from the group consisting of Table 1 perfumes A through G and an adjunct ingredient is also disclosed.

A consumer product comprising, based on total consumer product weight, from about 0.0001% to about 100% of a neat perfume selected from the group consisting of Table 1 perfumes A through G, the balance of said consumer product comprising an adjunct ingredient, and/or a perfume delivery system comprising a one or more Table 1 perfume raw materials is also disclosed.

A cleaning and/or treatment composition comprising based on total composition weight, from about 0.0001% to about 25% of a perfume selected from the group consisting of Table 1 perfumes A through G and an adjunct ingredient is also disclosed.

A fabric and/or hard surface cleaning and/or treatment composition comprising, based on total composition weight, from about 0.00001% to about 25% of a perfume selected from the group consisting of Table 1 perfumes A through G and an adjunct ingredient is also disclosed.

A detergent comprising, based on total detergent weight, from about 0.00001% to about 25% of a perfume selected from the group consisting of Table 1 perfumes A through G and an adjunct ingredient is also disclosed.

A highly compacted consumer product comprising, based on total highly compacted consumer product composition weight, from about 0.00001% to about 25% of a perfume selected from the group consisting of Table 1 perfumes A through G and an adjunct ingredient is also disclosed.

A deodorant comprising, based on total deodorant weight, from about 0.01% to about 75% of an antimicrobial and a perfume selected from the group consisting of Table 1 perfumes A through G is also disclosed. In one aspect, said deodorant comprises, based on total deodorant weight, from about 10% to about 75% glycol.

An antiperspirant comprising based on total antiperspirant weight, from about 1% to about 25% of an aluminum salt antiperspirant active and a perfume selected from the group consisting of Table 1 perfumes A through G is also disclosed.

A body wash/shampoo comprising a perfume selected from the group consisting of Table 1 perfumes A through G and a miscellar phase and/or lamellar phase is also disclosed.

A lotion comprising a perfume selected from the group consisting of Table 1 perfumes A through G and a humectant is also disclosed. In one aspect, said humectant comprises glycerin.

A fabric care composition comprising a perfume selected from the group consisting of Table 1 perfumes A through G, said fabric care composition being selected from the group consisting of detergents, fabric softeners, and laundry additives,
a) said detergent being:
  (i) a liquid detergent comprising a material selected from an anti-redep polymer, an enzyme, a structurant and mixtures thereof;
  (ii) a powder or granule detergent comprising a material selected from the group consisting of an anti-redep polymer, an enzymes, a bleach and mixtures thereof;
  (iii) a unit dose comprising a material selected from the group consisting of an anti-redep polymer, an enzymes, a bleach, a soluble substrate/film and mixtures thereof;
b) said fabric softener being a liquid, powder or sheet comprising a fabric softener active and an optional structurant;
c) said laundry additive being:
  (i) a bleach additive comprising a material selected from the group consisting of hypochlorite, hydrogen peroxide and mixtures thereof;
  (ii) a pretreater comprising a material selected from the group consisting of an effervescent, a propellant and mixtures thereof; and
  (iii) an in-wash boosters comprising a material selected from the group consisting of an enzyme, a non-chlorine bleach and mixtures thereof
is also disclosed.

A home care composition comprising a perfume selected from the group consisting of Table 1 perfumes A through G, said home care composition being selected from the group consisting of an automatic dish washing composition, a hand dish washing composition, a hard surface cleaning composition and an air care composition,
a) said automatic dish washing composition being:
  (i) a liquid or gel comprising a material selected from an anti-redep polymer, an enzyme, a structurant, a shine/sheeting polymer and mixtures thereof;
  (ii) a powder or granule comprising a material selected from the group consisting of an anti-redep polymer, an enzyme, a bleach, a shine/sheeting polymer and mixtures thereof;
  (iii) a unit dose comprising a material selected from the group consisting of an anti-redep polymer, an enzymes, a bleach, a shine/sheeting polymer, a soluble substrate/film and mixtures thereof
b) said hand dish washing composition comprising a material selected from the group consisting of a anti-bacterial, a hand/skin softener, shine/sheeting polymers and mixtures thereof;
c) said hard surface cleaning composition comprising a material selected from the group consisting of an anti-bacterial, a strong acid, preferably selected from the group consisting of glycolic acid, citric acid and mixtures thereof, etc., a strong base, preferably selected from the group consisting of Na hydroxides, a Li hydroxide and mixtures thereof, an effervescent, a propellants, a shine/sheeting polymers and mixtures thereof;

d) an air care composition comprising a malodor control composition that comprises zinc, cyclodextrin, a propellant and/or mixtures thereof is also disclosed.

Air Care Devices

As the perfumes disclosed herein are not habituating, such perfumes may be used without resorting to switching the perfumes as is common in air care devices so that the consumer does not become habituated. The present invention relates to an apparatus for the delivery of a volatile material to the atmosphere. It is contemplated that the apparatus may be configured for use in a variety of applications to deliver volatile materials to the atmosphere. Suitable devices include those devices disclosed in USPA 2012/0228402 A1 and USPA 2010/0308130 A1 both publications which are herein expressly incorporated by reference.

For example, the apparatus may be configured for use with an energized device. An exemplary energized device may be an electrical heating device. More particularly, the device may be an electrical wall plug air freshener as described in U.S. Pat. No. 7,223,361; a battery powered heating device; or other heating devices (e.g. devices powered by chemical reactions such as catalyst fuel systems; solar powered devices, etc.). In such devices, the volatile material delivery engine may be placed next to the heating surface to diffuse the volatile material. The volatile material formula may be adjusted to include an overall lower vapor pressure formula.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/ heating systems (e.g. HVAC).

The apparatus may also be configured for use with an aerosol or non-aerosol air spray. In this embodiment, the delivery engine can deliver volatile materials upon user demand or programmed to automatically deliver volatile materials to the atmosphere.

The apparatus may also be configured for use with a fan to deliver volatile materials to the atmosphere.

In one aspect, an apparatus for delivering a volatile material comprising a delivery engine having a liquid reservoir for containing a volatile material comprising a single opening; a rupturable substrate enclosing the single opening; a rupture element; a collection basin in fluid communication with the liquid reservoir upon rupturing the rupturable substrate; and a breathable membrane enclosing the liquid reservoir, rupturable substrate, rupture element, and collection basin is disclosed. The breathable membrane has an evaporative surface area of about 2 $cm^2$ to about 35 $cm^2$ and has an average pore size of about 0.02 microns. The apparatus also comprises a housing for receiving and releasably engaging the delivery system. The housing has a rib for guiding the delivery engine and a notch for compressing the rupture element upon insertion of the delivery engine into the housing.

FIGS. 1-3 depict an air care device that is suitable for use with the perfumes and compositions disclosed herein. As shown in FIGS. 1-3, the device 20 comprises a housing 22, and the housing 22 is supported on an electrical outlet 24 by a plug 26 that is at least indirectly joined to the housing 22. The device 20 further comprises at least one container. In the embodiment shown in FIGS. 1-3, the device 20 comprises two containers 28 and 30. The containers 28 and 30 contain at least a first volatile composition 32 and a second volatile composition 34. The housing 22 may serve as a holder for the containers 28 and 30 and any of the other components of the device described below.

In one aspect, an air care device that comprises one chamber said chamber comprising a perfume and/or a perfume raw material disclosed herein is disclosed. In one aspect, an air care device that comprises more than one chamber, at least one of said chambers comprising a perfume and/or a perfume raw material disclosed herein is disclosed.

Perfume Delivery Systems

Certain perfume delivery systems, methods of making certain perfume delivery systems and the uses of such perfume delivery systems are disclosed in USPA 2007/ 0275866 A1. The perfumes and PRMs disclosed herein may be used in such perfume delivery systems. Such perfume delivery systems include:

I. Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "preloaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable micro-particles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccharides and nanolatexes may be combined with other PDTs, including other PAD systems such as PAD reservoir systems in the form of a perfume microcapsule (PMC). Polymer Assisted Delivery (PAD) matrix systems may include those described in the following references: US Patent Application 2004/0110648 A1 and U.S. Pat. No. 6,531,444.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in USPA 20050143282A1. Functionalized silicones may also be used as described in USPA 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in USPA 2005/0003980 A1.

b.) Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. Suitable capsule wall materials include, in addition to aminoplasts, polyvinyl alcohol, polyvinyl pyrrolidone, polyethylene glycol, polysaccharides and modified polysaccharides, gel forming proteins, modified celluloses such as carboxymethylcelluloses and hydroxyethylcelluloses, polyacrylates, polyureas, polyurethanes and mixtures thereof. The capsules may be further coated with an additional coating that can improve the deposition and/or retention of the capsule on the desired surface. Suitable coating materials include a cationic polymer selected from the group consisting of selected from the group consisting of poly saccharides, cationically modified starch, cationically modified guar, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide to the surface of the capsule to form a cationically coated polymer encapsulated material. Typical capsules have a diameter of 1 micron to 500 microns. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged.

II. Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a C Log P greater than about 2. Molecule-Assisted Delivery (MAD) may also include those described in U.S. Pat. No. 7,119,060.

III. Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

IV. Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines. Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one aspect, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another aspect, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an aspect, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another aspect, AAD and PAD systems may interact with other materials, such as anionic surfactants or polymers to form coacervate and/or coacervates-like systems. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. Suitable AAD systems as well as methods of making same may be found in U.S. Pat. No. 6,103,678.

V. Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2006/0263313 A1.

VI. Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in U.S. Pat. No. 6,458,754 B1.

VII. Inorganic Carrier Delivery System (ZIC): This technology relates to the use of porous zeolites or other inorganic materials to deliver perfumes. Perfume-loaded zeolite may b e used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situ s or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

VIII. Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may b e pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiffs Bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one aspect, the photo-pro-perfume releases a nitrogen-based pro-perfume when exposed to a light and/or moisture trigger. In another aspect, the nitrogen-based pro-perfume, released from the photo-pro-perfume, releases one or more PRMs selected, for example, from aldehydes, ketones (including enones) and alcohols. In still another aspect, the PPP releases a dihydroxy coumarin derivative. The light-triggered pro-perfume may also be an ester that releases a coumarin derivative and a perfume alcohol. In one aspect the pro-perfume is a dimethoxybenzoin derivative as described in USPA 2006/0020459 A1. In another aspect the pro-perfume is a 3',5'-dimethoxybenzoin (DMB) derivative that releases an alcohol upon exposure to electromagnetic radiation. In yet another aspect, the pro-perfume releases one or more low ODT PRMs, including tertiary alcohols such as linalool, tetrahydrolinalool, or dihydromyrcenol. Suitable pro-perfumes and methods of making same can be found in U.S. Pat. No. 7,018,978 B2.

a.) Amine Reaction Product (ARP): For purposes of the present application, ARP is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in U.S. Pat. No. 6,413,920 B1.

b.) Sulfur-containing Pro-perfume Compound

The embodiments of the perfumes disclosed herein can be used as the perfume component pro-perfume compounds that contain sulfur. The term "pro-perfume compound" herein refers to compounds resulting from the chemical bonding of perfume raw materials (PRMs) with materials that comprise sulfur. The pro-perfume compound can release the original PRM (i.e., pre-converted) upon exposure to a trigger such as water or light or atmospheric oxygen. Suitable methods of making the same can be found in U.S. Pat. No. 7,018,978.

Amounts of Perfumes and PRMs Used in Delivery Systems

In one aspect, the perfumes and PRM disclosed herein, including those in Table 1, and stereoisomers thereof are suitable for use, in perfume delivery systems at levels, based on total perfume delivery system weight, of from 0.001% to about 50%, from 0.005% to 30%, from 0.01% to about 10%, from 0.025% to about 5%, or even from 0.025% to about 1%.

In one aspect, the perfume delivery systems disclosed herein are suitable for use in consumer products, cleaning and treatment compositions and fabric and hard surface cleaning and/or treatment compositions, detergents, and highly compacted consumer products, including highly compacted fabric and hard surface cleaning and/or treatment compositions, for example highly compacted detergents that may be solids or fluids, at levels, based on total consumer product weight, from about 0.001% to about 20%, from about 0.01% to about 10%, from about 0.05% to about 5%, from about 0.1% to about 0.5%.

In one aspect, the amount of the perfumes and PRM disclosed herein, including those Table 1 PRMs, based on the total microcapsules and/or nanocapsules (Polymer Assisted Delivery (PAD) Reservoir System) weight, may be from about 0.1% to about 99%, from 25% to about 95%, from 30 to about 90%, from 45% to about 90%, from 65% to about 90%.

In one aspect, the amount of total perfume based on total weight of starch encapsulates and starch agglomerates (Starch Encapsulated Accord (SEA)) ranges from 0.1% to about 99%, from 25% to about 95%, from 30 to about 90%, from 45% to about 90%, from 65% to about 90%. In one aspect, the perfumes and PRM disclosed herein, including those disclosed in Table 1, and stereoisomers thereof are suitable for use, in such starch encapsulates and starch agglomerates. Such perfumes, PRMs and stereoisomers thereof may be used in combination in such starch encapsulates and starch agglomerates.

In one aspect, the amount of total perfume based on total weight of [cyclodextrin—perfume] complexes (Cyclodextrin (CD)) ranges from 0.1% to about 99%, from 2.5% to about 75%, from 5% to about 60%, from 5% to about 50%, from 5% to about 25%. In one aspect, the perfumes and PRM disclosed herein, including those disclosed in Table 1, and stereoisomers thereof are suitable for use in such [cyclodextrin—perfume] complexes. Such perfumes, PRMs and stereoisomers thereof may be used in combination in such [cyclodextrin—perfume] complexes.

In one aspect, the amount of total perfume based on total weight of Polymer Assisted Delivery (PAD) Matrix Systems (including Silicones) ranges from 0.1% to about 99%, from 2.5% to about 75%, from 5% to about 60%, from 5% to about 50%, from 5% to about 25%. In one aspect, the amount of total perfume based on total weight of a hot melt perfume delivery system/perfume loaded plastic Matrix System and ranges from 1% to about 99%, from 2.5% to about 75%, from 5% to about 60%, from 5% to about 50%, from 10% to about 50%. In one aspect, the perfumes and PRM disclosed herein, including those disclosed in Table 1, and stereoisomers thereof, are suitable for use, in such Polymer Assisted Delivery (PAD) Matrix Systems, including hot melt perfume delivery system/perfume loaded plastic Matrix Systems. Such perfumes, PRMs and stereoisomers thereof may be used in combination in such Polymer Assisted Delivery (PAD) Matrix Systems (including hot melt perfume delivery system/perfume loaded plastic Matrix Systems).

In one aspect, the amount of total perfume based on total weight of Amine Assisted Delivery (AAD) (including Aminosilicones) ranges from 1% to about 99%, from 2.5% to about 75%, from 5% to about 60%, from 5% to about 50%, from 5% to about 25%. In one aspect, the perfumes and PRM disclosed herein, including those disclosed in Table 1, and stereoisomers thereof are suitable for use, in such Amine Assisted Delivery (AAD) systems.

In one aspect, the amount of total perfume based on total weight of Pro-Perfume (PP) Amine Reaction Product (ARP) system ranges from 0.1% to about 99%, from about 1% to about 99%, from 5% to about 90%, from 10% to about 75%, from 20% to about 75%, from 25% to about 60%. In one aspect, the perfumes and PRM disclosed herein, including those disclosed in Table 1, and stereoisomers thereof are suitable for use, in such Pro-Perfume (PP) Amine Reaction Product (ARP) systems.

The perfume delivery technologies also known as perfume delivery systems that are disclosed in the present specification may be used in any combination in any type of consumer product, cleaning and/or treatment composition, fabric and hard surface cleaning and/or treatment composition, detergent, and highly compact detergent.

In one aspect, an encapsulate comprising a shell and a core, said shell encapsulating said core and said core comprising a perfume and/or perfume raw disclosed herein, is disclosed.

In one aspect, an encapsulate comprising shell and a core, said core comprising a perfume selected from the group consisting of the perfumes and PRM disclosed herein, including those in Table 1 A through G, is disclosed.

In one aspect, of the encapsulates provided in the aspects above, said encapsulates' shells may comprise:
  (i) an aminoplast polymer, in one aspect, said aminoplast polymer comprises a material selected from the group consisting of a reaction product of melamine and formaldehyde, a reaction product of urea and formaldehyde and mixtures thereof, in one aspect, a material selected from the group consisting of methylol melamine, methylated methylol melamine, dimethylol urea, methylated dimethylol urea and mixtures thereof
  (ii) a material selected from the group consisting of a polyacrylate, a polyethylene glycol acrylate, a polyurethane acrylate, an epoxy acrylate, a polymethacrylate, a polyethylene glycol methacrylate, a polyurethane methacrylate, an epoxy methacrylate and mixtures thereof;
  (iii) a reaction product of one or more aromatic alcohols and one or materials comprising at least one aldehyde moiety in one aspect said aromatic alcohols may be phenols that comprise two or more hydroxyl groups, in one aspect, said aromatic alcohols are selected from the group consisting of brenzcatechin (pyrocatechol), resorcinol, hydroquinone, 1,4 naphthohydroxyquinone, phloroglucinol, pyrogallol, hydroxyhydroquinone and mixtures thereof. In one aspect, said materials comprising one or more aldehyde moieties comprise two, three, or four free aldehyde moieties per molecule, in one aspect, said materials comprising one or more aldehyde moieties is selected from the group consisting of glyoxal, gluteraldehyde, succindialdehyde; and/or
  (iv) the reaction product of melamine or a methylenediamine which has the structure $CH_2(NH_2)_2$, a material comprising one or more aldehyde moieties, an alkoxy ethanol and an acid, in one aspect, said material comprising one or more aldehyde moieties is selected from the group consisting of glyoxal, a C(4,6)-2,2-dialkoxy-ethanal, in one aspect, 2,2-dimethoxy-ethanal, or 2,2-diethoxy-ethanal, or mixtures thereof, a glyoxalate and mixtures thereof.

In one aspect, a cyclic oligosaccharide complex comprising a beta-cyclodextrin that is complexed with a perfume and/or perfume raw disclosed herein, is disclosed.

A cyclic oligosaccharide complex comprising a beta-cyclodextrin that is complexed with a perfume selected from the group consisting of the perfumes and PRM disclosed herein, including those Table 1 perfumes A through G, is also disclosed.

Adjunct Ingredients

For the purposes of the present invention, the non-limiting list of adjuncts illustrated hereinafter are suitable for use in the instant compositions and may be desirably incorporated in certain aspects of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems. The precise nature of these additional components, and levels of incorporation thereof, will depend on the physical form of the composition and the nature of the operation for which it is to be used. Suitable additional materials include, but are not limited to, bleach activators, antimicrobial, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, structure elasticizing agents, fabric softeners, carriers, hydrotropes, antiperspirant actives, processing aids and/or pigments. In addition to the disclosure below, suitable examples of such other adjuncts and levels of use are found in U.S. Pat. No. 6,326,348 B1.

Each adjunct ingredients is not essential to Applicants' compositions. Thus, certain embodiments of Applicants' compositions do not contain one or more of the following adjuncts materials: bleach activators, antimicrobial, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, structure elasticizing agents, fabric softeners, carriers, hydrotropes, antiperspirant actives, processing aids and/or pigments. However, when one or more adjuncts are present, such one or more adjuncts may be present as detailed below:

Antimicrobials—Suitable antimicrobials can include, but are not limited to, metals (e.g., Zn, Cu, Al, Ti, Sn, Bi, and Ag), metal salts (e.g., zinc carbonate, copper sulfate, and zinc gluconate), metal pyrithione salts (e.g., ZPT and CuPT), zeolites, metal zeolites, quaternary ammonium (quat) compounds (e.g., cetyl pyridinium chloride, and benzylalkonium chloride), quat bound clays, metal bound clays, and PolyAspirin. Other suitable antimicrobials can include salicylic acid, polyvinyl amines, coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulfide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), Glycols (such as propylene glycol; dipropylene glycol & hexylene glycol); diols (such as hexanediol), triclosan, triclocarban, isothiazalinones such as octyl isothiazalinone and azoles, and combinations thereof. Suitable antibacterial agents are described in U.S. Pat. No. 6,488,943 and U.S. Patent Application Publication No. 2008/0138441.

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known. Such cobalt catalysts are readily prepared by known procedures, such as taught for example in U.S. Pat. No. 5,597,936.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in U.S. Pat. No. 6,225,464.

The antiperspirant active for use in the anhydrous antiperspirant compositions of the present invention may include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Method of Use and Use

Certain of the consumer products disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

In one aspect, a method of reducing fragrance habituation comprising optionally washing and/or rinsing a situs, contacting said situs with any composition disclosed herein that comprises a perfume and/or perfume raw disclosed herein and mixtures thereof and optionally washing and/or rinsing and/or drying said situs, is disclosed.

In addition to the disclosure above, a method of reducing fragrance habituation comprising:
  a) optionally washing and/or rinsing a situs;
  b) contacting said situs with the any composition comprising a perfume selected from the group consisting of Table 1 perfumes A through G and/or a perfume selected from the group consisting of Table 1 perfumes A through G and mixtures thereof; and
  c) optionally washing and/or rinsing and/or drying, in one aspect via lined drying and/or machine drying, said situs
is disclosed.

In one aspect, the use of one or more perfume raw materials disclosed herein to impart ant-habituation properties to a perfume and/or consumer product that results in an improved freshness over time of such perfume and/or consumer is disclosed.

In one aspect, the use of one or more perfume raw materials disclosed herein to impart ant-habituation properties to a perfume and/or consumer product that results in an improved freshness over time of such perfume and/or consumer, wherein such perfume raw materials are selected from the group consisting of
  a) perfume raw materials comprising a thiol moiety is selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; Ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2-thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl)prop-1-ene; 3-sulfanylbutan-2-one;

ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl) propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propylsulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo[3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; 2-methyl-2-sulfanylpentan-1-ol; and mixtures thereof;

b) perfume raw materials comprising a sulfide moiety is selected from the group consisting of 1-butylsulfanylbutane; ethyl 3-methylsulfanylpropanoate; 2-(methylsulfanylmethyl)furan; methylsulfanylmethane; methyl sulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-yl sulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methyl sulfanylacetate; S-prop-2-enylpropanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl)methanethioate; 1,2,4-trithiolane; 2-methylthiolan-3-one; 4-methylsulfanylbutan-1-ol; S-butan-2-yl3-methylbutanethioate; S-butan-2-yl3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methyl sulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate and mixtures thereof;

c) perfume raw materials comprising a thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; 4-methyl-2-propan-2-yl-1,3-thiazole; and mixtures thereof;

d) said perfume raw material comprising a pyrazine moiety is selected from the group consisting of 2-methoxy-3-(2-methylpropyl)pyrazine; 2,3-dimethylpyrazine; 1-pyrazin-2-ylethanone; 2-methyl-3-methylsulfanylpyrazine; Pyrazine; 2-methylpyrazine; 2-ethenylpyrazine; 2-ethylpyrazine; 2,6-dimethylpyrazine; 2,5-dimethylpyrazine; 2-prop-1-en-2-ylpyrazine; 2-propan-2-ylpyrazine; 2-methoxypyrazine; 2-ethenyl-5-methylpyrazine; 2-ethyl-5-methylpyrazine; 2-Ethyl-6-methylpyrazine; 2-Ethyl-3-Methyl-Pyrazine; 2-propylpyrazine; 2,3,5-trimethylpyrazine; 2-tert-butylpyrazine; pyrazin-2-amine; 2-(2-methylpropyl)pyrazine; 2-methyl-5-propan-2-ylpyrazine; 2-(methoxymethyl)pyrazine; 2,3-diethylpyrazine; 2-ethyl-3,(5 OR 6)-dimethylpyrazine; 2-ethyl-3,5-dimethylpyrazine; 3-ethyl-2,5-dimethylpyrazine; 3-ethyl- 2,5-dimethylpyrazine; 2-ethyl-3,5-dimethylpyrazine; 2-methyl-3-propylpyrazine; 2,3,5,6-tetramethylpyrazine; 7-methyl-6,7-dihydro-5H-cyclopenta[b]pyrazine; 2-methylsulfanylpyrazine; 2-methyl-3-methylsulfanylpyrazine; 2-ethoxy-3-ethylpyrazine; 2-Isobutyl-3-methylpyrazine; pyrazin-2-ylmethanethiol; 3,5-dimethyl-2-propylpyrazine; 2-ethyl-3-methoxypyrazine; 2-ethoxy-3-methylpyrazine; 2-ethyl-5-methoxypyrazine; 5,6,7,8-tetrahydroquinoxaline; 2-ethoxy-3-propan-2-yl pyrazine; 2-(methylsulfanylmethyl)pyrazine; 3,5-dimethyl-2-(2-methylpropyl)pyrazine; 2,3-diethyl-5-methylpyrazine; 3,5-Diethyl-2-methylpyrazine; 2,5-dimethyl-3-(2-methylpropyl)pyrazine; 2-methyl-6-propoxypyrazine; 2-(2-methylpropoxy)pyrazine; 1-(3-methylpyrazin-2-yl)ethanone; 2-methyl-3-methylsulfanylpyrazine; 2-methoxy-3-propan-2-ylpyrazine; quinoxaline; 3-butyl-2,5-dimethylpyrazine; 2-butyl-3,5-dimethylpyrazine; 2-pyrazin-2-ylethanethiol; 1-(3-ethylpyrazin-2-yl)ethanone; 1-(3,5-dimethylpyrazin-2-yl)ethanone; 2-butan-2-yl-3-methoxypyrazine; 2-methylquinoxaline; 5-Methylquinoxaline; 2-methoxy-3-(4-methylpentyl)pyrazine; 2,3-dimethylquinoxaline; 2-(cyclohexylmethyl)pyrazine; 2-[(furan-2-ylmethyl)sulfanyl]-5-methylpyrazine and mixtures thereof;
e) perfume raw materials comprising a nitrile moiety is selected from the group consisting of 3,7-dimethyloct-6-enenitrile, 3-(4-ethylphenyl)-2,2-dimethylpropanenitrile; and mixtures thereof;
f) perfume raw materials comprising a indole moiety is selected from the group consisting of 1H-indole, 3-methyl-1H-indole; and mixtures thereof;
g) perfume raw materials comprising a oxathiane moiety is selected from the group consisting of (2R,4S)-2-methyl-4-propyl-1,3-oxathiane, 2-methyl-4-propyl-1,3-oxathiane, 2-pentyl-4-propyl-1,3-oxathiane; and mixtures thereof;
h) perfume raw materials comprising a oxime moiety is selected from the group consisting of (NE)-N-[(6E)-2,4,4,7-tetramethylnona-6,8-dien-3-ylidene]hydroxylamine; N-(5-methylheptan-3-ylidene)hydroxylamine, and mixtures thereof;
i) perfume raw materials comprising a amine moiety is selected from the group consisting of methyl 2-aminobenzoate, pentane-1,5-diamine; 6-methyl-7-Oxa-1-thia-4-azaspiro[4.4]nonane; and mixtures thereof;

In one aspect, said perfume raw materials comprise at least one sulfur, oxygen and nitrogen atom, said perfume raw material being selected from the group consisting of 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1(1,3-thiazol-2-yl)propan-1-one; 1-(2,4-dimethyl-1,3-thiazol-5-yl)ethanone; 2-amino-4-methyl sulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid; and mixtures thereof;

In one aspect:
a) said perfume raw materials comprising a thiol moiety is selected from the group consisting of 5-methyl-5-sulfanylhexan-3-one; 2-(4-methyl-1-cyclohex-3-enyl)propane-2-thiol; 5-methyl-2(2-sulfanylpropan-2-yl)cyclohexan-1-one; 4,7,7-trimethyl-6-thiabicyclo[3.2.1]octane; 4-methoxy-2-methylbutane-2-thiol; and mixtures thereof;
b) said perfume raw materials comprising a sulfide moiety is selected from the group consisting of 1-butylsulfanylbutane; ethyl 3-methylsulfanylpropanoate; 2-(methylsulfanylmethyl)furan; and mixtures thereof;
c) said perfume raw materials comprising a thiazole moiety is selected from the group consisting of 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; 1-(1,3-thiazol-2-yl)ethanone; and mixtures thereof;
d) said perfume raw materials comprising a pyrazine moiety is selected from the group consisting of 2-methoxy-3-(2-methylpropyl)pyrazine; 2,3-dimethylpyrazine; 1-pyrazin-2-ylethanone; 2-methyl-3-methylsulfanylpyrazine; and mixtures thereof;
e) said perfume raw materials comprising a nitrile moiety is selected from the group consisting of 3,7-dimethyloct-6-enenitrile, 3-(4-ethylphenyl)-2,2-dimethylpropanenitrile; and mixtures thereof;
f) said perfume raw materials comprising a indole moiety is selected from the group consisting of 1H-indole.
g) said perfume raw materials comprising a oxathiane moiety is selected from the group consisting of (2R,4S)-2-methyl-4-propyl-1,3-oxathiane.
h) said perfume raw materials comprising a oxime moiety is selected from the group consisting of (NE)-N-[(6E)-2,4,4,7-tetramethylnona-6,8-dien-3-ylidene]hydroxylamine.
i) said perfume raw materials comprising a amine moiety is selected from the group consisting of methyl 2-aminobenzoate, pentane-1,5-diamine, 6-methyl-7-Oxa-1-thia-4-azaspiro[4.4]nonane; and mixtures thereof;
j) said perfume raw materials comprising oxygen, sulfur, and nitrogen is selected from the group consisting of 2-(4-methyl-1,3-thiazol-5-yl)ethanol, 1-(1,3-thiazol-2-yl)ethanone; 6-methyl-7-Oxa-1-thia-4-azaspiro[4.4]nonane; and mixtures thereof;

In one aspect, said perfume raw material comprises perfume raw materials selected from the group consisting of:
a) 1-butylsulfanylbutane; (2R,4S)-2-methyl-4-propyl-1,3-oxathiane; and 4-methoxy-2-methylbutane-2-thiol;
b) (NE)-N-[(6E)-2,4,4,7-tetramethylnona-6,8-dien-3-ylidene]hydroxylamine; and 7-hydroxy-3,7-dimethyloctanal; 3-(4-ethylphenyl)-2,2-dimethylpropanenitrile;
c) 2-(4-methyl-1,3-thiazol-5-yl)ethanol; 7-Oxa-1-thia-4-azaspiro[4.4]nonane; and 6-methyl-, 1-(1,3-thiazol-2-yl)ethanone;
d) 2-methoxy-3-(2-methylpropyl)pyrazine; 1-pyrazin-2-ylethanone; and 2,3-dimethylpyrazine;
e) 2-(methylsulfanylmethyl)furan; ethyl 3-methylsulfanylpropanoate; and 1-butylsulfanylbutane;
f) 5-methyl-5-sulfanylhexan-3-one; 5-methyl-2-(2-sulfanylpropan-2-yl)cyclohexan-1-one; and 2-(4-methyl-1-cyclohex-3-enyl)propane-2-thiol;
g) 2-methoxy-3-(2-methylpropyl)pyrazine; 3,7-dimethyl-oct-6-enenitrile; and methyl 2-aminobenzoate;
h) 2-(2-methylpropyl)-1,3-thiazole; 2-(4-methyl-1,3-thiazol-5-yl)ethanol; and 4-methyl-2-propan-2-yl-1,3-thiazole;
i) (2R,4S)-2-methyl-4-propyl-1,3-oxathiane; 2-(4-methyl-1-cyclohex-3-enyl)propane-2-thiol; and (NE)-N-[(6E)-2,4,4,7-tetramethylnona-6,8-dien-3-ylidene]hydroxylamine; and
j) mixtures thereof;
is disclosed.

In one aspect, a method to enhance the fragrance profile of a composition, preferably improve the longevity of an aroma, preferably a floral aroma, of a composition, comprising bringing into contact or mixing at least one non-odorous fragrance modulator with at least one low volatile fragrance material according to a composition as defined herein previously is disclosed. In one aspect, said floral aroma is selected from the group consisting of a lavender-type note, a rose-type note, a lily of the valley type note, a muguet type note, a magnolia type note, a cyclamen type note, a hyacinth type note, a lilac type note, and combinations thereof.

In one aspect, a method for producing a consumer product comprising bringing into contact or mixing into the product an organoleptically active quantity of a perfume composition disclosed herein, said perfume composition comprising a fragrance modulator, is disclosed.

In one aspect, a method of modifying or enhancing the odour properties of a body surface, comprising contacting or treating the body surface with a perfume composition disclosed herein, said perfume composition comprising a fragrance modulator, is disclosed.

TEST METHODS

The Degree of Habituation to a perfume, PRM or product comprising such materials, is determined via human panel testing with daily exposures to the scent over a four week period, and is calculated at both the week two and week four time points, relative to the initial baseline time point.

For each exposure panel test, more than 15 panelists are recruited, then exposed to the test scent in a manner, frequency, and concentration indicated by the intended product end use, but including at least one exposure per day every day for four consecutive weeks. The perfume exposure must be sufficient that the panelists can detect the perfume of interest being delivered from the product or perfume delivery system contained within the product. The criteria for recruitment onto the exposure panel requires that panelists be typical consumers of the product in question, who agree to use the scent being tested, are non-smokers, and free of nasal congestion and allergies. The degree of habituation is calculated and reported as the percent change in the Odor Detection Threshold (ODT) value at week 2 and at week 4, versus the initial baseline ODT value. Since the degree of habituation is a relative measure, it accommodates the variation in absolute ODT values which can arise between different testing laboratories.

Raw materials and finished products comprising them may be used together in conjunction in order to determine the degree of habituation. For example, daily exposures to the panelists may involve the use of a finished product while the ODT test measurements may involve the use of the respective neat perfume or PRM. The conditions selected for use in either the daily exposures or in the ODT testing must be applied uniformly across all panelists, and remain unchanged for the entirety of the four week testing period. When the test perfume materials are available in their simple forms i.e., PRM, neat perfume, or fine fragrance, unincorporated into complex products or delivery systems, then the ODT test is to be conducted with these simple forms via an olfactometer, as this is the preferred method. When these simple forms of the test perfume materials are inaccessible for testing, then the ODT test may be conducted with finished products or complex formulations comprising the test perfume materials. Presentation devices other than an olfactometer may be required when conducting the ODT testing on finished products or complex formulations, and may include devices such as sniff cups, headspace chambers and capped bottles, as allowed for in the test method ASTM E679-04 described below.

The ODT value for each panelist is determined at each of three time points the during four week daily exposure period, namely; at initial baseline, at two weeks, and at four weeks. The ODT values are always to be determined in accordance with test method ASTM E679-04 (Standard Practice for Determination of Odor and Taste Thresholds by a Forced-Choice Ascending Concentration Series of Limits) as reapproved in 2011 except, the following replaces the protocol of such test method's Sub-articles 4.4, 8.2 and 8.3.

Sub-article 4.4, Individual best-estimate values of the threshold are derived from the pattern of correct/incorrect responses produced separately by each panelist. The group average ODT value at a given time point is derived by fitting the entire data set from all panelists at that time point to a Log Logistic Regression Model.

Sub-article 8.2, If the concentration range has been correctly selected, it is not necessary that all panelists judge correctly within the range of concentration steps provided. Thus, the representation of the panelists' judgments as in 8.1 need not terminate with two or more consecutive plusses (+).

Sub-article 8.3, Since there is a finite probability that a correct answer will occur by chance alone, it is important that a panelist repeat the test three times. Panelists who fail the test at the highest concentration, are deemed anosmic to the test material and their response is removed from the data set.

Additionally, the following selections are made in accordance with the test method's sub-articles 1.3, 1.4, 1.6, 1.7, and 4.1, and specified here as per sub-article 9.3.

Sub-article 1.3, The threshold is characterized as being a) only detection (awareness) that a very small amount of added substance is present but not necessarily recognizable.

Sub-article 1.4, When the preferred method is being conducted, namely using a simple perfume form presented via olfactometer, then the presentation medium can be an air, pure nitrogen, or a mixture of the two. When testing finished or complex products, alternative presentation media may be used, such as air.

Sub-article 1.6, When the preferred method is being conducted, namely using a simple perfume form presented via olfactometer, then the physical method of presentation is at a rate of 40 L/min.

When testing finished or complex products, alternative presentation devices may be used, including but not limited to sniff cups, headspace chambers or capped bottles.

Sub-article 1.7, Presentation is made to a panel of greater than 15 panelists, who are participating in the daily exposure panel.

Sub-article 4.1, Eight scale steps are used, with each step having an individual predetermined dilution factor suitable for the stimuli being tested, at a temperature of 35° C. PRM or neat perfume stimuli are typically introduced to the olfactometer system in the neat form via a pump syringe. Sometimes a dilution of the stimuli with ethanol is needed.

The group average ODT values from the three time points are used to calculate the degree of habituation. The degree of habituation is reported for 2 specific time points, as the percent change in group average ODT at one time point, relative to the group average ODT at the initial baseline time point. The degree of habituation is determined at the time points of: 2 weeks and 4 weeks, of the four week daily exposure period, using the following formula:

Degree of Habituation (percent change in ODT) at Time $X$=((Group Average $ODT_{(Time\ X)}$−Group Average $ODT_{(Baseline)}$)/Group Average $ODT_{Baseline}$)×100 where Time X is either 2 weeks, or 4 weeks, of repeated daily exposure.

Anti-habituation index

A perfume is considered to have an anti-habituation index of:

For a two week test

Zero (0) when the Degree of Habituation after 2 weeks of exposure to said perfume is from about 150% to 25%

One (1) when the Degree of Habituation after 2 weeks of exposure to said perfume is less than 25% but greater than 10%;

Two (2) when the Degree of Habituation after 2 weeks of exposure to said perfume is from 10% to 0%; or Three (3) when the Degree of Habituation after 2 weeks of exposure to said perfume is less than 0% to about −25%.

Four (4) when the Degree of Habituation after 2 weeks of exposure to said perfume is less than −25% to about −500%

For a four week test

Zero (0) when the Degree of Habituation after 4 weeks of exposure to said perfume is from about 150% to 25%

One (1) when the Degree of Habituation after 4 weeks of exposure to said perfume is less than 25% but greater than 10%;

Two (2) when the Degree of Habituation after 4 weeks of exposure to said perfume is from 10% to 0%; or Three (3) when the Degree of Habituation after 4 weeks of exposure to said perfume is less than 0% to about −25%.

Four (4) when the Degree of Habituation after 4 weeks of exposure to said perfume is less than −25% to about −500%

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Example Anhydrous Stick Compositions that resist habituation, excluding formula IV

| | Formula I Invisible Solid | Formula II Invisible Solid | Formula III Invisible Solid | Formula IV Soft Solid | Formula V Soft Solid | Formula VI Soft Solid |
|---|---|---|---|---|---|---|
| Aluminum Zirconium Trichlorohydrex Glycine Powder | 24 | 24 | 24 | 26.5 | 26.5 | 26.5 |
| Cyclopentasiloxane | Q.S | Q.S. | Q.S. | Q.S. | Q.S. | Q.S. |
| Dimethicone | — | — | — | 5 | 5 | 5 |
| CO-1897 Stearyl Alcohol NF | 14 | 14 | 14 | — | — | — |
| Hydrogenated Castor Oil MP80 Deodorized | 3.85 | 3.85 | 3.85 | — | — | — |
| Behenyl Alcohol | 0.2 | 0.2 | 0.2 | — | — | — |
| Tribehenin | — | — | — | 4.5 | 4.5 | 4.5 |
| C 18-36 acid triglyceride | — | — | — | 1.125 | 1.125 | 1.125 |
| C12-15 Alkyl Benzoate | 9.5 | 9.5 | 5 | — | — | — |
| PPG-14 Butyl Ether | 6.5 | 6.5 | — | 0.5 | 0.5 | 0.5 |
| Phenyl Trimethicone | 3 | — | 3 | — | — | — |
| White Petrolatum | 3 | — | — | 3 | 3 | 3 |
| Mineral Oil | 1.0 | 1.0 | 1.0 | — | — | — |
| Typical Perfume | 0.5 | — | — | 0.9 | — | — |
| Marketed Perfume | — | — | — | — | — | 0.75 |
| Perfume Table 1 | 0.5 | 1.1 | 0.9 | — | 1.0 | — |
| Beta-Cyclodextrin complexed with perfume Table 1 | — | 3.0 | — | — | — | 3.0 |
| Talc Imperial 250 USP | 3.0 | 3.0 | 3.0 | — | — | — |
| Polyacrylate Microcapsule loaded with perfume Table 1 | — | — | 1.9 | — | — | — |

QS-indicates that this material is used to bring the total to 100%.

With the exception of Formula IV, the formulations defined above contain perfume from table 1 at various levels, optionally using various perfume delivery systems. Formula III contains Perfume from Table 1 contained in a polyacrylate microcapsule, as described above in Polymer Assisted Deliver, Reservoir Systems. Formula VI contained perfume from table 1, as described above in Cyclodextrin Delivery Systems.

Test subjects were recruited for the following study, based on their acceptance of the scent of the products in formulas IV, V, and VI above. Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in three study groups with an antiperspirant/deodorant according to formulas IV, V, and VI and instructed to apply 2 clicks per underarm (approximately 0.4 g per underarm) throughout the four week study period, using no other underarm products throughout the duration of the study. Their Odor Detection Threshold (ODT) was measured again after 2 weeks of usage, and again after 4 weeks of usage. The average Odor Detection Threshold was calculated for each usage group. Results are shown below.

The results indicate that the Odor Detection Threshold increases significantly above baseline (test subjects are less sensitive) for the usage group using Formula IV (comparative perfume) after 4 weeks of usage, indicating habituation. The surprising result is that the Odor Detection Threshold remains below baseline for each usage group using formula V and formula VI that contain the perfume from table 1, indicating that they did not become habituated to the scent of the product over time. Therefore, the perfume used in formula V and VI is has an anti-habituation index of 4 and 3 respectively when tested in a two week test and an anti-habituation index of 4 and 4 respectively when tested in a four week test.

Degree of Habituation (% change in group average OPT) Results:

| Product Used | Type of Perfume Run in the ODT test | % Change in ODT at Week 2 | % Change in ODT at Week 4 |
|---|---|---|---|
| Formula IV from Example 1 | Comparative Perfume | 41% | 634% |
| Formula V from Example 1 | Perfume from Table 1 | −86% | −29% |
| Formula VI from Example 1 | Perfume from Table 1 | −24% | −91% |

Example 2

Anhydrous Stick Compositions that Resist Habituation

TABLE 2

Base Perfume Formulation PD

| Ingredient | Percent | CAS# |
|---|---|---|
| 2 6 Nonadienol 10% In DPG | 0.20% | |
| Allyl Amyl Glycolate | 0.10% | 67634-00-8 |
| Allyl Cyclohexane Propionate | 0.50% | 2705-87-5 |
| Allyl Heptoate | 1.00% | 142-19-8 |
| Ambrettolide | 0.50% | 28645-51-4 |
| Anisic Aldehyde | 0.10% | 123-11-5 |
| Benzaldehyde | 0.05% | 100-52-7 |
| Benzoin Siam Resinoid 50% Mpg Ref A | 0.20% | 9000-72-0 |
| Benzyl Acetate | 3.00% | 140-11-4 |
| Benzyl Salicylate | 5.00% | 118-58-1 |
| Beta Gamma Hexenol | 0.20% | 928-96-1 |
| Cashmeran | 0.20% | 33704-61-9 |
| Cinnamic Alcohol | 0.10% | 104-54-1 |
| Cis 3 Hexenyl Acetate | 0.30% | 3681-71-8 |
| Cis-3-Hexenyl Salicylate | 1.00% | 65405-77-8 |
| Cis-6-Nonen-1-OL FCC | 0.05% | 35854-86-5 |
| Citronellol | 0.30% | 106-22-9 |
| Citronellyl Acetate | 0.10% | 150-84-5 |
| Citronellyl Oxyacetaldehyde | 0.04% | 7492-67-3 |
| Cyclo Galbanate | 0.10% | 68901-15-5 |
| Cymal | 4.00% | 103-95-7 |
| Delta Damascone | 0.20% | 57378-68-4 |
| Delta Muscenone 962191 | 0.10% | 63314-79-4 |
| Dihydro Myrcenol | 2.00% | 18479-58-8 |
| Dimethyl Benzyl Carbinyl Acetate | 0.50% | 151-05-3 |
| Ethyl 2 Methyl Pentanoate | 0.30% | 39255-32-8 |
| Ethyl Acetoacetate | 0.50% | 141-97-9 |
| Ethyl Maltol | 0.40% | 4940-11-8 |
| Ethyl-2-Methyl Butyrate | 0.10% | 7452-79-1 |
| Ethylene Brassylate | 7.00% | 105-95-3 |
| Floralozone | 0.50% | 67634-15-5 |
| Gamma Decalactone | 0.50% | 706-14-9 |
| Geranyl Acetate | 0.20% | 105-87-3 |
| Helional | 1.00% | 1205-17-0 |
| Heliotropin | 0.10% | 120-57-0 |
| Hexamethylindanopyran | 10.00% | 1222-05-5 |
| Hexyl Acetate | 0.50% | 142-92-7 |
| Hexyl Cinnamic Aldehyde | 7.00% | 101-86-0 |
| Hydroxycitronellal | 3.00% | 107-75-5 |
| Indolene | 0.20% | 68908-82-7 |
| Ionone Gamma Methyl | 5.00% | 127-51-5 |
| Iso E Super Or Wood | 10.00% | 54464-57-2 |
| Iso Eugenol | 0.05% | 97-54-1 |
| Jasmolactone | 0.10% | 32764-98-0 |
| Laevo Trisandol | 2.00% | 28219-61-6 |
| Liffarome | 0.40% | 67633-96-9 |
| Ligustral Or Triplal | 0.20% | 68039-49-6 |
| Linalool | 5.00% | 78-70-6 |
| Linalyl Acetate | 3.00% | 115-95-7 |
| Lyral | 2.00% | 31906-04-4 |
| Melonal | 0.20% | 106-72-9 |
| Methyl Dihydro Jasmonate | 10.00% | 24851-98-7 |
| Methyl Pamplemousse | 0.30% | 67674-46-8 |
| Methyl Phenyl Carbinyl Acetate | 0.40% | 93-92-5 |
| Methyl-2-Nonenoate | 0.10% | 111-79-5 |
| Nerolidol | 0.50% | 7212-44-4 |
| Oil Lemon Brazilcp Select Fcc Enh 15130 | 1.00% | 8008-56-8 |
| Orivone | 0.20% | 16587-71-6 |
| Para Hydroxy Phenyl Butanone | 1.00% | 5471-51-2 |
| Phenyl Ethyl Alcohol | 0.50% | 60-12-8 |
| Phenyl Ethyl Phenyl Acetate | 0.05% | 102-20-5 |
| Pino Acetaldehyde | 0.05% | 33885-51-7 |
| Polysantol | 0.20% | 107898-54-4 |
| Precyclemone B | 0.30% | 52475-86-2 |
| Prenyl Acetate | 0.20% | 1191-16-8 |
| Prunella | 0.10% | |
| Synambran R 50% In IPM* | 0.20% | |
| Undecalactone | 2.00% | 104-67-6 |
| Undecavertol | 0.50% | 81782-77-6 |
| Undecylenic Aldehyde | 0.01% | 112-44-7 |
| Vanillin | 0.30% | 121-33-5 |
| Verdox | 3.00% | 88-41-5 |

*Supplied by Symrise GmbH, with offices located at Muhlenfeldstrasse 1, Holzminden, 37603, Germany

TABLE 3

Control Perfume Formulation PD with additional perfume raw materials

| | Perfume 2.A | Perfume 2.B | Perfume 2.C | Perfume 2.D |
|---|---|---|---|---|
| Base Control Perfume Formulation PD from Table 2 | 99.9987% | 98.99999% | 99.94% | 93.5% |
| 5-Mercapto-5-Methyl-3-hexanone | 0.001% | | | |
| P-Mentha-8-Thiol-3-One | 0.00025% | | | |
| 1-para-menthene-8-thiol | 0.00005% | | | |
| 2-methoxy-3-(2-methylpropyl)pyrazine | | 0.00001% | | |
| 3,7-dimethyloct-6-enenitrile | | 0.5% | | |
| methyl 2-aminobenzoate | | 0.5% | | |
| 2-(4-methyl-1,3-thiazol-5-yl)ethanol | | | 0.05% | |
| 2-(2-methylpropyl)-1,3-thiazol | | | 0.005% | |
| 4-methyl-2-propan-2-yl-1,3-thiazole | | | 0.005% | |
| (1R,2S,5R)-5-methyl-2-propan-2-ylcyclohexan-1-ol | | | | 5.0% |
| [(1R,2S,5R)-5-methyl-2-propan-2-ylcyclohexyl]acetate | | | | 1.0% |
| (2R,5R)-5-methyl-2-(propan-2-yl)cyclohexanone | | | | 0.5% |

TABLE 4

Soft Solid Antiperspirant Compositions

| | Formula VII Soft Solid | Formula VIII Soft Solid | Formula IX Soft Solid | Formula X Soft Solid | Formula XI Soft Solid |
|---|---|---|---|---|---|
| Aluminum Zirconium Trichlorohydrex Glycine Powder | 26.5 | 26.5 | 26.5 | 26.5 | 26.5 |
| Cyclopentasiloxane | Q.S. | Q.S. | Q.S. | Q.S. | Q.S. |
| Dimethicone | 5 | 5 | 5 | 5 | 5 |
| Tribehenin | 4.5 | 4.5 | 4.5 | 4.5 | 4.5 |
| C 18-36 acid triglyceride | 1.125 | 1.125 | 1.125 | 1.125 | 1.125 |
| PPG-14 Butyl Ether | 0.5 | 0.5 | 0.5 | 0.5 | 0.5 |
| White Petrolatum | 3 | 3 | 3 | 3 | 3 |
| Base Control Perfume Formulation | 0.8 | — | — | — | — |
| Perfume 2.A | — | 0.8 | — | — | — |
| Perfume 2.B | — | — | 0.8 | — | — |
| Perfume 2.C | — | — | — | 0.8 | — |
| Perfume 2.D | — | — | — | — | 0.8 |

QS-indicates that this material is used to bring the total to 100%.

The formulations defined above various perfume formulations. Formula VII contains a base control perfume formulation PD. Formulas VIII, IX, X, and XI each contain additional components. More specifically, formula VIII containing Perfume 2.A includes a three component perfume accord composed of perfume raw materials containing a thiol moiety. Formula IX containing Perfume 2.B includes a three component perfume accord composed of perfume raw materials containing pyrazine, nitrile and amine moieties. Formula X containing Perfume 2.0 includes a three component perfume accord composed of perfume raw materials containing a thiazole moiety. Formula XI containing Perfume 2.D includes a three component perfume accord composed of perfume raw materials consisting of menthol and menthol derivatives.

Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in five study groups with an antiperspirant/deodorant according to formulas VII, VIII, IX, X, and XI and instructed to apply 2 clicks per underarm (approximately 0.4 g per underarm) throughout the four week study period, using no other underarm products throughout the duration of the study. Their Odor Detection Threshold (ODT) was measured again after 2 weeks of usage, and again after 4 weeks of usage. The average Odor Detection Threshold was calculated for each usage group. Results are shown below.

The results indicate that the Odor Detection Threshold remains unchanged for the usage group using Formula VII (comparative perfume) after 4 weeks of usage. The Odor Detection Threshold increases significantly above baseline (test subjects are less sensitive) for the usage group using Formula XI (perfume containing menthol and menthol derivatives) after 4 weeks of usage, indicating habituation. One surprising result is that the base perfume's (Formula VII) anti-habituation index of two (2) from the two week test moved, when antihabituation materials were added (formulations VIII, IX and X) to an anti-habituation indices for such formulas of, 4, 4 and 3 respectively under the two week test when the additional perfume raw materials(s) as specified in Perfume 2.A, Perfume 2.B and Perfume 2.0 are added. Another surprising result is that the base perfume's (Formula VII) anti-habituation index of three (3) from the four week test moved, when antihabituation materials were added (formulations VIII, IX and X) to an anti-habituation indices for such formulas of, 4, 4 and 4 respectively under the four week test when the additional perfume raw materials(s) as specified in Perfume 2.A, Perfume 2.B and Perfume 2.0 are added. Such materials were a thiol accord, pyrazine-nitrile-amine accord, and thiazole accord.

TABLE 5

Degree of Habituation (% change in group average ODT) Results:

| Product Used | Type of Perfume Run in the ODT Test | % Change in ODT at Week 2 | % Change in ODT at Week 4 |
|---|---|---|---|
| Formula VII | Base Perfume Formulation PD | 2% | -2% |
| Formula VIII | Perfume 2.A- Base Control Perfume Formulation PD comprising Thiol Accord | -86% | -93% |
| Formula IX | Perfume 2.B- Base Control Perfume Formulation PD comprising pyrazine-nitrile-amine Accord | -94% | -90% |
| Formula X | Perfume 2.C Base Control Perfume Formulation PD comprising Thiazole Accord | -6% | -62% |
| Formula XI | Perfume 2.D Base Control Perfume Formulation PD comprising menthol and menthol derivative Accord | 96% | 1052% |

The above formulations VII, VIII, IX, X, and XI were rated by consumers in a usage test. 10 independent test groups of approximately 20 panelists were instructed to use the product as they normally would. 5 of the test groups, each using one of the formulas VII, VIII, IX, X, and XI were instructed to use the product for a single day, and rate their overall opinion of the product after using the product based on a 5 point scale. (100=Excellent, 75=Very Good, 50=Good, 25=Fair, 0=Poor). Separately, the other 5 test groups, each using one of the formulas VII, VIII, IX, X, and XI were instructed to use the product for a four week period, and rate their overall opinion of the product based on the same 5 point scale defined above. Results indicate that formulas are rated parity after a single day usage, but the resistance to habituation shown in table 5 yields an improved usage rating, only after a four week period.

TABLE 6

|  | Formula VII | Formula VIII | Formula IX | Formula X | Formula XI |
| --- | --- | --- | --- | --- | --- |
| Overall Rating Single Day Use | 64 | 57 | 60 | 65 | 66 |
| Overall Rating 4 Week Use | 66 | 69 | 75 | 80 | 70 |
| Delta of single day vs. 4 week ratings | +2 | +12 | +15 | +15 | +4 |

Example 3

Anhydrous Stick Compositions that Resist Habituation

TABLE 7

Soft Solid Antiperspirant Compositions

|  | Formula XII Soft Solid | Formula XIII Soft Solid | Formula XIV Soft Solid |
| --- | --- | --- | --- |
| Aluminum Zirconium Trichlorohydrex Glycine Powder | 26.5 | 26.5 | 26.5 |
| Cyclopentasiloxane | Q.S. | Q.S. | Q.S. |
| Dimethicone | 5 | 5 | 5 |
| Tribehenin | 4.5 | 4.5 | 4.5 |
| C 18-36 acid triglyceride | 1.125 | 1.125 | 1.125 |
| PPG-14 Butyl Ether | 0.5 | 0.5 | 0.5 |
| White Petrolatum | 3 | 3 | 3 |
| Beta-Cyclodextrin complexed with perfume |  |  | 3 |
| Perfume (defined in following table) | 0.9 | — | — |
| Comparative Perfume A | — | 0.9 | — |
| Comparative Perfume C | — | — | 1.5% |

QS-indicates that this material is used to bring the total to 100%.

TABLE 8

| Example Number | Base Perfume Formulation PD Level from Table 2 | Anti-habituating Material | CAS Number of Anti-habituating Material | Percent of Anti-habituating Material in perfume |
| --- | --- | --- | --- | --- |
| XII.A | 100% | — | — | — |
| XII.B | 99.998 | Sauvignone 100* | 851768-51-9 | 0.00002 |
| XII.C | 99.98 | Sauvignone 100* | 851768-51-9 | 0.0002 |
| XII.D | 99.8 | Sauvignone 100* | 851768-51-9 | 0.002 |
| XII.E | 99.5 | 4,7,7-trimethyl-6-thiabicyclo[3.2.1]octane | 68398-18-5 | 0.5 |
| XII.F | 99.998 | 1-butylsulfanyl-butane | 544-40-1 | 0.002 |
| XII.G | 99.98 | 1-butylsulfanyl-butane | 544-40-1 | 0.02 |
| XII.H | 99.9 | 1-(1,3-thiazol-2-yl)ethanone | 24295-03-2 | 0.1 |
| XII.I | 99.98 | (2R,4S)-2-methyl-4-propyl-1,3-oxathiane | 59323-76-1 | 0.02 |
| XII.J | 99.9 | (2R,4S)-2-methyl-4-propyl-1,3-oxathiane | 59323-76-1 | 0.2 |
| XII.K | 99.9975 | 2-methyl-3-methylsulfanyl-pyrazine | 67952-65-2 | 0.0025 |
| XII.L | 99.99 | 1-pyrazin-2-ylethanone | 22047-25-2 | 0.01 |
| XII.M | 99.5 | 3,7-dimethyloct-6-enenitrile | 51566-62-2 | 0.5 |
| XII.N | 99.7 | 1H-indole | 120-72-9 | 0.3 |
| XII.O | 99.6 | Labienoxime ** | 81783-01-9 | 0.04 |
| XII.P | 99.9999 | 2-methoxy-3-(2-methylpropyl)-pyrazine | 24683-00-9 | 0.0001 |
| XII.Q | 99.9998 | 2-methoxy-3-(2-methylpropyl)pyrazine | 24683-00-9 | 0.0002 |

*Sauvignone 100 is supplied as a 1% active containing 5-methyl-5-sulfanylhexan-3-one
** Labienxoxime is supplied as a 10% active containing (NE)-N-[(6E)-2,4,4,7-tetramethylnona-6,8-dien-3-ylidene]hydroxylamine The formulations defined in Table 8 are various perfume formulations to be used in Formula XII. Seventeen unique formulas were made from Formula XII, each containing 0.9% of one of the perfumes from example number XII.A through XII.Q, as defined in Table 8.

Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in nineteen study groups with an antiperspirant/deodorant and instructed to apply 2 clicks per underarm (approximately 0.4 g per underarm) throughout the four week study period, using no other underarm products throughout the duration of the study. Their Odor Detection Threshold (ODT) was measured again after 4 weeks of usage. The average Odor Detection Threshold was calculated for each usage group. Results are shown below.

The results indicate that the Odor Detection Threshold increases significantly above baseline (test subjects are less sensitive) for the usage group using the formula containing the base perfume PD only, which was void of all sulfur and nitrogen PRM's after 4 weeks of usage, indicating habituation. Surprisingly, all components containing sulfur or nitrogen chemistry showed improvement relative to the control. The data further suggests that molecules containing sulfur or nitrogen having a sulfide moiety, thiazole moiety, oxime moiety, or acetyl group produce the highest resistance to habituation, therefore have the highest anti-habituation index at levels below and above threshold

TABLE 9

Degree of Habituation (% change in group average ODT) Results:

| Product Used | Pink Daisy Perfume + Antihabituating material defined below for ODT Test | Chemical Moiety of Anti-habituating Material | % Change in ODT at Week 4 | Anti-habituation Index for four week test |
|---|---|---|---|---|
| Formula XII containing XII.A | — | | 3554 | Highly Habituating, thus no index |
| Formula XII containing XII.B | Sauvignone 100 (below threshold) | Thiol | 166 | Habituating, thus no index |
| Formula XII containing XII.C | Sauvignone 100 (above threshold) | Thiol | 728 | Habituating, thus no index |
| Formula XII containing XII.D | Sauvignone 100 (saturation point) | Thiol | 364 | Habituating, thus no index |
| Formula XII containing XII.E | 4,7,7-trimethyl-6-thiabicyclo[3.2.1]octane (above threshold) | Sulfide | −61 | 4 |
| Formula XII containing XII.F | 1-butyl-sulfanylbutane (below threshold) | Sulfide | −63 | 4 |
| Formula XII containing XII.G | 1-butyl-sulfanylbutane (above threshold) | Sulfide | −31 | 4 |
| Formula XII containing XII.H | 1-(1,3-thiazol-2-yl)ethanone (above threshold) | Thiazole | −59 | 4 |
| Formula XII containing XII.I | (2R,4S)-2-methyl-4-propyl-1,3-oxathiane (below threshold) | Oxathiane | 413 | Habituating, thus no index |
| Formula XII containing XII.J | (2R,4S)-2-methyl-4-propyl-1,3-oxathiane (above threshold) | Oxathiane | 218 | Habituating, thus no index |
| Formula XII containing XII.K | 2-methyl-3-methylsulfanyl-pyrazine (above threshold) | Pyrazine comprising a Sulfide moiety | −88 | 4 |
| Formula XII containing XII.L | 1-pyrazin-2-ylethanone (above threshold) | Pyrazine comprising an acetyl moiety | −84 | 4 |
| Formula XII containing XII.M | 3,7-dimethyloct-6-enenitrile (above threshold) | Nitrile | 221 | Habituating, thus no index |
| Formula XII containing XII.N | 1H-indole (above threshold) | Indole | 208 | Habituating, thus no index |
| Formula XII containing XII.O | Labienoxime (above threshold) | Oxime | −69 | 4 |
| Formula XII containing XII.P | 2-methoxy-3-(2-methylpropyl)pyrazine (below threshold) | Pyrazine | 110 | 0 |
| Formula XII containing XII.Q | 2-methoxy-3-(2-methylpropyl)pyrazine (above threshold) | Pyrazine | 339 | Habituating, thus no index |
| Formula XIII | Contains Comparative Perfume A Only | | 111 | 0 |
| Formula XIV | Contains Comparative Perfume C Only | | 405 | Habituating, thus no index |

It is believed that the differences seen from Example 2, in which the base perfume had an anti-habituation index of 3 in the four week test, vs. Example 3, in which the base perfume had significant increase in ODT is beyond what is expected of individual variation among panelists and were related to the difference in perfume level (0.8% vs. 0.9%). Further, it is believed that the base perfume would be habituating, even at a lower perfume level if the test subjects used the product for a longer duration. The addition of sulfur and nitrogen PRM's consistently showed greater resistance to habituation as compared to the control—regardless of perfume level tested.

Example 4

TABLE 10

Example Body Wash Compositions

| | Formula XV Body Wash | Formula XVI Body Wash | Formula XVII Body Wash |
|---|---|---|---|
| Sodium Laureth-3 Sulfate (as 28% active) | 27.85% | 27.85% | 27.85% |
| Water | Q.S. | Q.S. | Q.S. |
| Sodium Lauryl Sulfate (as 29% active) | 10.34 | 10.34 | 10.34 |
| Cocamidopropyl Betaine B (30% active) | 4.01 | 4.01 | 4.01 |
| Citric Acid | 0.18 | 0.18 | 0.18 |
| Sodium Benzoate | 0.3 | 0.3 | 0.3 |
| Disodium EDTA | 0.12 | 0.12 | 0.12 |
| Methylchloro-isothiazolinone/Methylisothiazolinone | 0.04 | 0.04 | 0.04 |
| Sodium Chloride | 2.35% | 1.7% | 1.6% |
| Comparative Perfume A | 1.25% | — | — |
| Comparative Perfume B | — | 1.25% | — |
| Perfume Table 1 | — | — | 1.25% |

QS-indicates that this material is used to bring the total to 100%.

The formulations defined above contain various perfume formulations. Formula XVII contains Perfume from Table 1. Formula XV and XVI contain comparative perfumes.

Approximately 20 test subjects per usage group were recruited for the study. The test subjects placed in the study were assessed for their baseline threshold intensity according to the Odor Detection Threshold (ODT) method defined above for the perfume of interest that was in the product. Test subjects were placed in three study groups with a body wash according to formulas XV, XVI, and XVII and instructed to use the product daily, as they normally would use their current cleansing product throughout the four week study period, using no other cleansing products throughout the duration of the study. Their Odor Detection Threshold (ODT) was measured again after 2 weeks of usage, and again after 4 weeks of usage. The average Odor Detection Threshold was calculated for each usage group. Results are shown below.

The results indicate that the Odor Detection Threshold increases significantly above baseline (test subjects are less sensitive) for the usage group using Formula XV (comparative perfume A) after 4 weeks of usage, indicating habituation. The surprising result is that the test group using the body wash containing the perfume from table 1 had the lowest degree of habituation after 4 weeks of usage, indicating that they did not become habituated to the scent of the product over time. Therefore, the perfume used in formula XVII is has an anti-habituation index of 0 when tested in a two week test and an anti-habituation index of 4 when tested in a four week test.

TABLE 11

Degree of Habituation (% change in group average ODT) Results:

| Product Used | Type of Perfume Run in the ODT test | % Change in ODT at Week 2 | % Change in ODT at Week 4 |
|---|---|---|---|
| Formula XV from Example 3 | Comparative Perfume A | 554% | 2948% |
| Formula XVI from Example 3 | Comparative Perfume B | −73% | −4% |
| Formula XVII from Example 3 | Perfume from Table 1 | 121 | −93% |

Example 2

Preformed Amine Reaction Product

The following ingredients are weighted off in a glass vial:
50% of the perfume material comprising one or more off the perfumes claimed herein, for example, Table 1 perfumes A through G
50% of Lupasol WF (CAS #09002-98-6) from BASF, is put at 60° C. in warm water bath for 1 hour before use. Mixing of the two ingredients is done by using the Ultra-Turrax T25 Basic equipment (from IKA) during 5 minutes. When the mixing is finished the sample is put in a warm water bath at 60° C. for ±12 hours. A homogenous, viscous material is obtained. In the same way as described above different ratios between the components can be used:

| | Weight % | | | | |
|---|---|---|---|---|---|
| Perfume Material | 40 | 50 | 60 | 70 | 80 |
| Lupasol WF | 60 | 50 | 40 | 30 | 20 |

Example 3

84 wt % Core/16 wt % Wall Melamine Formaldehyde (MF) Capsule (PAD Reservoir System 25 grams of butyl acrylate-acrylic acid copolymer emulsifier (Colloid C351, 25% solids, pka 4.5-4.7, (Kemira Chemicals, Inc. Kennesaw, Georgia U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, New Jersey, U.S.A.)) is added to the emulsifier solution. 200 grams of one or more off the perfumes claimed herein, for example, Table 1 perfumes A through G is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Missouri, U.S.A.) is added to the suspension. An average capsule size of 30 um is obtained as analyzed by a Model 780 Accusizer.

Example 4

Process of Making a Polymer Assisted Delivery (PAD) Matrix System

A mixture comprising 50% of one or more off the perfumes claimed herein, for example, Table 1 perfumes A through G, 40% of carboxyl-terminated Hycar®1300X18 (CAS #0068891-50-9) from Noveon, (put at 60° C. in warm water bath for 1 hour before mixing) and 10% of Lupasol® WF(CAS #09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| | Weight % | | | | |
|---|---|---|---|---|---|
| Table 1 Perfume | 40 | 50 | 60 | 70 | 80 |
| Lupasol ® WF | 12 | 10 | 8 | 6 | 4 |
| Hycar ® CTBN1300X18 | 48 | 40 | 32 | 24 | 16 |

| | Weight % | | | | | | | |
|---|---|---|---|---|---|---|---|---|
| Perfume composition | 50 | 50 | 50 | 50 | 50 | 50 | 50 | 50 |
| Lupasol ® WF | 2.5 | 5 | 7.5 | 10 | 12.5 | 15 | 17.5 | 20 |
| Hycar ® CTBN 1300X18 | 47.5 | 45 | 42.5 | 40 | 37.5 | 35 | 32.5 | 30 |

Example 5

Product Formulation—Fabric Softener

Non-limiting examples of product formulations containing PRMs disclosed in the present specification perfume and amines summarized in the following table.

| (% wt) | XI | XII | XIII | XIV | XV | XVI | XVII | XVIII | XIX | XX |
|---|---|---|---|---|---|---|---|---|---|---|
| FSA [a] | 14 | 16.47 | 14 | 12 | 12 | 16.47 | — | — | 5 | 5 |
| FSA [b] | | | | | | | 3.00 | — | | |
| FSA [c] | | | | | — | | — | 6.5 | | |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Amine* | 0.6 | 0.75 | 0.6 | 0.75 | 0.37 | 0.60 | 0.37 | 0.6 | 0.37 | 0.37 |
| Perfume X [e] | 0.40 | 0.13 | 0.065 | 0.25 | 0.03 | 0.030 | 0.030 | 0.065 | 0.03 | 0.03 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Additional Adjunct Perfume | 0.8 | 0.7 | 0.9 | 0.5 | 1.2 | 0.5 | 1.1 | 0 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl)N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[e] Perfume from Table 1.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculan 44.
*One or more materials comprising an amine moiety as disclosed in the present specification.
† balance

Example 6

Dry Laundry Formulations

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphoric acid) | 0.4 | 0.4 | 0.4 | 0.4 | 0.4 | 0.4 | 0.4 |

-continued

| Component | % w/w granular laundry detergent composition | | | | | | |
|---|---|---|---|---|---|---|---|
| | A | B | C | D | E | F | G |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Additional Adjunct Perfume** | 0.5 | 0.5 | 0.5 | 0.5 | 0.5 | 0.5 | 0.5 |
| Amine* | 0.1 | 0.5 | 0.0 | 0.01 | 0.02 | 0.00 | 0.07 |
| Perfume Delivery System As Disclosed In The Present Specification Including Examples 2-4 | 0.05 | 0.0 | 0.1 | 0.0 | 0.2 | 0.4 | 0.0 |
| Perfume Table 1 | 0.3 | 0.4 | 0.01 | 0.02 | 0.04 | 0.1 | 0.1 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*One or more materials comprising an amine moiety as disclosed in the present specification.
**Optional

Example 7

Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |

-continued

| Ingredient | HDL 1 | HDL 2 | HDL3 | HDL4 | HDL 5 | HDL 6 |
|---|---|---|---|---|---|---|
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Additional Adjunct | 0.7 | 0.5 | 0.8 | 0.6 | 0.6 | 0.5 |
| Perfume** | | | | | | |
| Amine* | 0.01 | 0.10 | 0.0 | 0.10 | 0.20 | 0.05 |
| Perfume from Table 1 | 0.02 | 0.15 | 0.10 | 0.2 | 0.3 | 0.05 |
| Perfume Delivery System As Disclosed In The Present Specification Including Examples 2-4 | 0.2 | 0.02 | 0.4 | 0.0 | 0.0 | 0.0 |
| Water | Balance | Balance | Balance | Balance | Balance | Balance |

*One or more materials comprising an amine moiety as disclosed in the present specification.
**Optional.

Example 8

Deodorant Compositions

| Ingredient | VI | VII | VIII | IX | X |
|---|---|---|---|---|---|
| Product Form | Solid Deodorant | Solid Deodorant | Solid Deodorant | Solid Deodorant | Aerosol Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Perfume Table 1 | 0.5 | 1.0 | 1.0 | 0.5 | 1.5 |
| Propellant (1,1 difluoroethane) | | | | | 40 |

QS-indicates that this material is used to bring the total to 100%.

Shampoo Compositions

| EXAMPLE COMPOSITION | 20 | 21 |
|---|---|---|
| Ammonium Laureth Sulfate (AE$_3$S) | 6.00 | 6.00 |
| Ammonium Lauryl Sulfate (ALS) | 10.00 | 10.00 |
| Laureth-4 Alcohol | 0.90 | 0.90 |
| Trimethylammoniopropylmethacrylamide chloride-N-Acrylamide copolymer [25] | 0.25 | — |
| Trihydroxystearin [7] | 0.10 | 0.10 |
| Perfume Table 1 | 0.60 | 0.60 |
| Sodium Chloride | 0.40 | 0.40 |
| Citric Acid | 0.04 | 0.04 |
| Sodium Citrate | 0.40 | 0.40 |
| Sodium Benzoate | 0.25 | 0.25 |
| Ethylene Diamine Tetra Acetic Acid | 0.10 | 0.10 |
| Dimethicone [9, 10, 11] | 1.00 [9] | 1.00 [9] |
| Water and Minors | Q.S. | Q.S. |

Lotion Example

| | Example 1 | Example 2 | Example 3 |
|---|---|---|---|
| Water Phase: | | | |
| Water | qs | qs | qs |
| Glycerin | 5.0 | 5.0 | 5.0 |
| Disodium EDTA | 0.1 | 0.1 | 0.1 |
| Methylparaben | 0.2 | 0.2 | 0.2 |
| Niacinamide | 4.0 | 4.0 | 4.0 |
| D-panthenol | 0.5 | 0.5 | 0.5 |
| Phenylbenzimidazole Sulfonic Acid | 1.0 | 1.0 | 1.0 |
| Pentylene Glycol | 1.0 | 1.0 | 1.0 |
| Benzyl alcohol | 0.25 | 0.25 | 0.25 |
| Triethanolamine | 0.64 | 0.64 | 0.64 |
| Oil Phase: | | | |
| Isopropyl Isostearate | 1.33 | 1.33 | 1.33 |
| Octisalate | 4.0 | 4.0 | 4.0 |
| Octocrylene | 1.0 | 1.0 | — |
| Avobenzone | 2.0 | 2.0 | — |
| Petrolatum | 2 | 2 | 2 |
| Shea Butter | 0.5 | 0.5 | 0.5 |
| Vitamin E Acetate | 0.1 | 0.1 | 0.1 |
| Ethylparaben | 0.2 | 0.2 | 0.2 |
| Propylparaben | 0.2 | 0.2 | 0.2 |
| Cetyl alcohol | 0.3 | 0.3 | 0.3 |
| Stearyl alcohol | 0.4 | 0.4 | 0.4 |
| Behenyl alcohol | 0.4 | 0.4 | 0.4 |
| Cetearyl Glucoside/Cetearyl Alcohol[1] | 0.3 | 0.3 | 0.3 |
| PEG-100 stearate | 0.3 | 0.3 | 0.3 |
| Tinosorb S[5] | — | 1 | 2 |
| Synovea DOI[6] | 4.0 | 5.0 | 6.0 |
| Thickener: | | | |
| Sepigel ™ 305[2] | 2.25 | 2.25 | 2.25 |
| Additional Ingredients: | | | |
| Perfume Table 1 | 1.0 | 0.75 | 1.25 |
| Microthene FN510[3] | 1.0 | 1.0 | 1.0 |

-continued

|  | Example 1 | Example 2 | Example 3 |
|---|---|---|---|
| Polysorbate 20 | 0.5 | 0.5 | 0.5 |
| Dow Corning ™ 1503[4] | 2.0 | 2.0 | 2.0 |
| Total: | 100% | 100% | 100% |

[1]Emulgade ™ PL68/50 from Cognis ™
[2]Polyacrylamide, C13-14 isoparaffin, and laureth-7 from Seppic ™
[3]Polyethylene homopolymer spheres from Equistar ™
[4]Dimethicone and dimethiconol from Dow Corning ™
[5]Bis-Ethylhexyloxyphenol Methoxyphenyl Triazine from BASF ™
[6]Dioctanoyl Isosorbide from Syntheon ™

In a suitable vessel, the water phase ingredients are combined and heated to 75° C. In a separate suitable vessel, the oil phase ingredients are combined and heated to 75° C. Next the oil phase is added to the water phase and the resulting emulsion is milled (eg., with a Tekmar T-25). The thickener is then added to the emulsion and the emulsion is cooled to 45° C. while stirring. At 45° C., the remaining additional ingredients are added. The product is then cooled with stirring to 30° C., milled again, and then poured into suitable containers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fabric care composition selected from the group consisting of:
   a) a liquid detergent comprising a liquid detergent material selected from an anti-redeposition polymer, an enzyme, a structurant, or mixtures thereof,
   b) a powder or granule detergent comprising a powder or granule detergent material selected from the group consisting of an anti-redeposition polymer, an enzyme, a bleach, and mixtures thereof,
   c) a unit dose comprising a unit dose material selected from the group consisting of an anti-redeposition polymer, an enzyme, a bleach, a soluble substrate, and mixtures thereof;
   d) a fabric softener being a liquid, powder or sheet comprising a fabric softener active and an optional structurant;
   e) a laundry additive being selected from the group consisting of:
      (i) a bleach additive comprising a bleach additive material selected from the group consisting of hypochlorite, hydrogen peroxide, and mixtures thereof,
      (ii) a pretreater comprising a pretreater material selected from the group consisting of an effervescent, a propellant, and mixtures thereof,
      (iii) an in-wash booster comprising an in-wash booster material selected from the group consisting of an enzyme, a non-chlorine bleach and mixtures; and
      (iv) mixtures thereof, and
   f) and mixtures thereof,
      wherein the fabric care composition further comprises from 0.00000001% to 0.1%, based on the total weight of the fabric care composition, of a perfume raw material comprising a sulfide moiety selected from the group consisting of 1-butylsulfanylbutane; ethyl 3-methylsulfanylpropanoate; 2-(methylsulfanylmethyl)furan; methylsulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enyl propanethioate; 1-methylsulfanylbutan-2-one; 4-methylsulfanylbutan-2-one; 3-methylsulfanylpropan-1-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S-propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl) methanethioate; 1,2,4-trithiolane; 2-methylthiolan-3-one; 4-methylsulfanylbutan-1-ol; S-butan-2-yl 3-methylbutanethioate; S-butan-2-yl 3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; 2-methyl-3-methylsulfanylpyrazine; ethyl 3-(furan-2-ylmethylsulfanyl)propanoate; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate and mixtures thereof, wherein the perfume raw material is present below its odor detection threshold, and wherein the perfume raw material is in the core of a microcapsule.

2. The composition of claim 1, wherein the fabric care composition has:
a) a two week anti-habituation index of at least 0;
b) a four week anti-habituation index of at least 0;
c) a two week anti-habituation index of 0, 1, 2, 3, or 4; and/or
d) a four week anti-habituation index of 0, 1, 2, 3, or 4.

3. The composition of claim 1 further comprising a perfume delivery system comprising the perfume raw material comprising the sulfide moiety.

4. The composition of claim 1, wherein the microcapsule further comprises a shell,
wherein the shell comprises a shell material selected from the group consisting of aminoplasts, polyvinyl alcohol, polyvinyl pyrrolidone, polyethylene glycol, polysaccharides, modified polysaccharides, gel forming proteins, polyacrylates, polyureas, polyurethanes, and mixtures thereof.

5. The composition of claim 4, wherein the shell material comprises aminoplasts.

6. The composition of claim 5, wherein the shell material comprises urea-formaldehyde and/or melamine-formaldehyde.

7. The composition of claim 4, wherein the shell material comprises polyvinyl alcohol.

8. The composition of claim 4, wherein the shell material comprises polysaccharides, modified polysaccharides, or mixtures thereof.

9. The composition of claim 4, wherein the shell material comprises gel forming proteins.

10. The composition of claim 4, wherein the shell material comprises polyacrylates.

11. The composition of claim 4, wherein the shell material comprises polyureas, polyurethanes, or mixtures thereof.

12. The composition of claim 1, wherein the microcapsules are gelatin-based.

13. The composition of claim 1, wherein the microcapsules are further coated with an additional coating.

14. The composition of claim 13, wherein the additional coating comprises a coating material selected from the group consisting of polysaccharides, cationically modified starch, cationically modified guar, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide, and mixtures thereof.

15. The composition of claim 13, wherein the additional coating is a cationic coating.

16. The composition of claim 1, wherein the microcapsules are characterized by a diameter of from 1 micron to 500 microns.

17. The composition of claim 1, wherein the microcapsules are formed by a procedure that includes coating, extrusion, spray-drying, interfacial polymerization, in-situ polymerization, matrix polymerization, or combinations thereof.

18. The composition of claim 1, wherein the fabric care composition is a fabric softener.

19. The composition of claim 18, wherein the fabric softener is a liquid.

20. The composition of claim 19, wherein the fabric softener comprises a structurant.

* * * * *